United States Patent [19]
Meyer, Jr. et al.

[11] Patent Number: 5,849,482
[45] Date of Patent: Dec. 15, 1998

[54] CROSSLINKING OLIGONUCLEOTIDES

[75] Inventors: Rich B. Meyer, Jr., Bothell; Howard B. Gamper, Woodinville; Igor V. Kutyavin; Alexander A. Gall, both of Bothell; Charles R. Petrie, Woodinville; John C. Tabone, Bothell, all of Wash.; Gerald D. Hurst, The Woodlands, Tex.

[73] Assignee: Epoch Pharmaceuticals, Inc., Bothell, Wash.

[21] Appl. No.: 485,611

[22] Filed: Jun. 7, 1995

Related U.S. Application Data

[63] Continuation-in-part of Ser. No. 226,949, Jun. 27, 1994, Ser. No. 334,490, Nov. 4, 1994, and Ser. No. 178,733, Jan. 7, 1994, abandoned, said Ser. No. 226,949, is a continuation-in-part of Ser. No. 11,482, Jan. 26, 1993, abandoned, said Ser. No. 334,490, is a continuation of Ser. No. 49,807, Apr. 20, 1993, abandoned, which is a continuation of Ser. No. 353,857, May 18, 1989, abandoned, which is a continuation-in-part of Ser. No. 250,474, Sep. 28, 1988, abandoned, said Ser. No. 178,733, is a continuation of Ser. No. 748,138, Aug. 21, 1991, abandoned, which is a continuation-in-part of Ser. No. 353,857, which is a continuation-in-part of Ser. No. 250,474.

[51] Int. Cl.$^6$ .............................. C12Q 1/68; C07H 21/04
[52] U.S. Cl. .............................. 435/6; 536/23.1; 536/24.3
[58] Field of Search .............................. 514/44; 536/24.3, 536/24.5, 24.31, 24.32, 18.4, 124, 23.1; 435/6, 172.1, 172.3, 375; 436/94, 183

[56] References Cited

PUBLICATIONS

H. Moser et al Science 238 (Oct. 30, 1987) 645–650.
J. Hartley et al. Biochem. 29 ('90) 2985–91.
V. Vlassov et al. Gene 72 ('88) 313–22.
E. Uhlmann et al. Chem. Rev. 90(4) ('90) 543–84.
J. Milligan et al. J. Med. Chem. 36(14) ('93) 1926–37.
C. Srein et al. Science 261 (Aug. 1993) 1004–12.
B. Tseng et al Cancer Gene Ther. 1(1) (94) 65–71.
T. Brown et al., in Oligontides and Analogues, A. Practical Approach, Ed. F. Eckstein, IRL Press, Oxford U.K., 1991, pp. 1–24.
L. Pauling Chem. & Eng. News 24(10):1375–7 ('46).
R. Dickerson et al. The Stnc. & Action of Protis. Benjamin/Cumming Publ. Co., Menlo Park, CA, 1969, p. 68.

*Primary Examiner*—John L. LeGuyader
*Attorney, Agent, or Firm*—Klein & Szekeres, LLP

[57] ABSTRACT

Oligonucleotides (ODNs) include a sequence that is complementary to a target sequence in single stranded RNA, or single or double stranded DNA, and an alkylating function which after hybridization alkylates the target sequence. ODNs adapted for alkylating single stranded RNA, such as messenger RNA, are complementary to the target sequence in the Watson Crick sense. ODNs adapted for alkylating double stranded DNA have at least two alkylating functions and are complementary to the target sequence in the Hoogsteen or reverse Hoogsteen sense. With these ODNs both strands of the target sequence are alkylated. A third class of ODNs have at least approximately 26 nucleotide units in a continous sequence which are complementary to the target sequence of double stranded DNA, and the alkylating function is covalently attached to a nucleotide unit in the continuous sequence. Alkylation or cross-linking with this class of ODNs occurs in the presence of a recombinase enzyme.

6 Claims, No Drawings

CROSSLINKING OLIGONUCLEOTIDES

CROSS-REFERENCE TO RELATED APPLICATIONS

The present application is
(1) a continuation-in-part of application Ser. No. 08/226,949 filed on Jun. 27, 1994, pending, which is a continuation-in-part of application Ser. No. 08/011,482, filed on Jan. 26, 1993 now abandoned;
(2) a continuation-in-part of application Ser. No. 08/334,490 filed on Nov. 4, 1994, pending, which is a continuation of application Ser. No. 08/049,807 filed on Apr. 20, 1993, now abandoned, which is a continuation of application Ser. No. 07/353,857 filed on May 18, 1989, now abandoned, which is a continuation-in-part of application Ser. No. 250,474 filed on Sep. 28, 1988 now abandoned;
(3) a continuation-in-part of application Ser. No. 08/178,733 filed on Jan. 7, 1994, now abandoned, which is a continuation of application Ser. No. 07/748,138 filed on Aug. 21, 1991, now abandoned, which is a continuation-in-part of application Ser. No. 07/353,857 filed on May 18, 1989, now abandoned, which is a continuation-in-part of application Ser. No. 07/250,474 filed on Sep. 28, 1988, now abandoned.

BACKGROUND OF THE INVENTION

1. Field of the Invention

The present invention is directed to oligonucleotides which have a cross-linking agent covalently attached to one or more nucleotide units, and are capable of binding either by classic Watson Crick or by Hoogsteen or reverse Hoogsteen pairing to a target sequence of DNA or RNA. The cross-linking oligonucleotides of the present invention can be utilized for therapeutic, diagnostic, DNA mapping and similar investigative or analytical purposes.

2. Description of the Prior Art

Oligodeoxynucleotides (ODNs) have great potential as sequence specific pharmaceutical agents for the inhibition of gene expression. Chemically synthesized ODNs may inhibit the expression of specific gene products through formation of duplexes upon hybridization with complementary messenger RNAs (mRNAs). More specifically, these "antisense" ODNs are believed to inhibit the processing or translation of message primarily through an RNase H-mediated cleavage of the target mRNA sequence. Because of this inhibitory effect, antisense ODNs may be useful as anti-viral, anti-parasitic, and anti-cancer agents. However, "antisense" technology is beset with certain fundamental disadvantages relating, for example, to degradation of antisense ODNs by nuclease enzymes, and uptake (or lack of uptake) by cells. To improve their properties, modified antisense ODNs, such as ODNs with modified backbones (oligonucleoside methylphosphonates and phosphorothioates) have been prepared. It has been found however, that improvement in some properties, such as resistance to nuclease enzymes frequently has deleterious effects on other properties, such as cellular uptake and loss of specificity.

Another approach to improve the effectiveness of antisense ODNs involves covalently attaching moieties to the antisense ODNs which moieties interact directly with the target RNA upon hybridization and therefore potentiate the antisense activity of the ODN. Groups employed in this regard are intercalating groups, and groups which covalently link with the target RNA after hybridization.

Anti-gene ODNs

A variation of the "antisense" approach to rational drug design is termed "anti-gene". Whereas antisense ODNs target single stranded MRNA, anti-gene ODNs hybridize with and are capable of inhibiting the function of double-stranded DNA. More specifically, anti-gene ODNs form sequence-specific triple-stranded complexes with a double stranded DNA target and thus interfere with the replication or transcription of selected target genes. As is known, except for certain RNA viruses and nucleic acid-free viroids, DNA is the repository for all genetic information, including regulatory control sequences and non-expressed genes, such as dormant proviral DNA genomes. In contrast, the target for antisense ODNs, MRNA, represents a very small subset of the information encoded in DNA. Thus, anti-gene ODNs have broader applicability and are potentially more powerful than antisense ODNs that merely inhibit mRNA processing and translation.

Anti-gene ODNs in the nuclei of living cells can form sequence-specific complexes with chromosomal DNA. The resultant triplexes have been shown to inhibit restriction and/or transcription of the target double stranded DNA. Based on the known stabilities of the two target nucleic acid species (i.e., DNA and RNA), anti-gene interference with DNA functioning has longer lasting effects than the corresponding antisense inhibition of mRNA function.

As noted above, anti-gene therapy may be based on the observation that under certain conditions DNA can form triple-stranded complexes. In these triple-stranded complexes, the third strand resides in the major groove of the Watson-Crick base paired double helix, where it hydrogen bonds to one of the two parental strands. A binding code governs the recognition of base pairs by a third base (see allowed triplets below, Hoogsteen or reverse Hoogsteen pairing). In each case, the third strand base is presented first and is followed by the base pair in the Watson-Crick duplex.

allowed triplets:  A—A—T    G—G—C
                   T—A—T    C—G—C

Certain limitations of this base pair recognition code are apparent from the allowed triplets. First, there is no capability for the recognition of T—A and C—G base pairs; hence, triple strand formation is restricted to runs of purine bases on one strand and pyrimidine bases on the other strand of the duplex. In other words, the third strand or ODN binds only to one strand of the duplex and can only bind to purines. Second, if cytosine is in the third strand ("C"), it must be protonated to be able to hydrogen bond to the guanine of a G—C base pair. The pKa for protonation of cytosine is 4.6, suggesting that at physiological pH the stability of C—G—C triads is likely to be impaired. Third, in all cases triads are maintained by two hydrogen bonds between the third strand base and the purine residue of the duplex base pair. Hence, triple-stranded complexes are generally less stable than the parental double-stranded DNA, which is maintained by a combination of two (A—T) or three (G—C) hydrogen bonds between purine and pyrimidine pairs. (Watson-Crick motif).

An important disadvantage of triple strand formation as discussed above is the relatively slow kinetics of triple strand formation. However, triple strand formation can be catalyzed in cells by recombinase enzymes which are practically ubiquitous in cells and whose existence is well known in the art. In addition to a much faster rate of triple strand formation, recombinase enzyme-catalyzed triple strand formation also provides the advantage of universal sequence recognition (in contrast to the A—T and G—C recognition limitation associated with non-enzyme-mediated triple strand formation). More specifically, the recombinase enzyme-mediated recognition motif recognizes all four base pairs, thereby allowing targeting of any double stranded DNA sequence. Second, the nucleoprotein filament, which is the complex formed between a recombinase enzyme and the single-stranded ODN, searches for target double strand DNA homology much more efficiently than does a small naked anti-gene ODN, thus decreasing the concentration of anti-gene ODN required for efficient triple strand complex formation. Third, due to the hydrogen bonding patterns and the novel helical twist involved in enzyme-mediated recognition, the resultant triple strand complex is stable at physiological pH. Fourth, since the cellular recombinational pathway is being harnessed, the DNA in higher order chromatin structures will be accessible for targeting.

A first demonstration of the concept of using sequence-specific, antisense oligonucleotides as regulators of gene expression and as chemotherapeutic agents was described by Zamecnik and Stephenson, *Proc. Natl. Acad. Sci. USA*, 75:280 (1978). These authors showed that a small antisense oligodeoxynucleotide probe can inhibit replication of Rous Sarcoma Virus in cell culture, and that RSV viral RNA translation is inhibited under these conditions (Stephenson et al., *Proc. Natl. Acad. Sci. USA* 75:285 (1978)). Zamecnik et al., *Proc. Natl. Acad. Sci. USA*, 83:4143 (1986), have also shown that oligonucleotides complementary to portions of the HIV genome are capable of inhibiting protein expression and virus replication in cell culture. Inhibition of up to 95% was obtained with oligonucleotide concentrations of about 70 $\mu$M. Importantly, they showed with labeled phosphate studies that the oligonucleotides enter cells intact and are reasonably stable to metabolism.

The concept of covalently linking an inhibitor molecule to a target (such as binding an ODN to an target sequence with a cross-linking arm,) is related to the pioneering work of B. R. Baker, "Design of Active-Site-Directed Irreversible Enzyme Inhibitors," Wiley, N.Y., (1967), who used what was termed "active-site-directed enzyme inhibitors" in chemotherapeutic applications. The concept of incorporating a crosslink in an oligonucleotide has been sporaidically discussed by several authors. For example, Knorre and Vlassov, *Prog. Nucl. Acid Res. Mol. Biol.*, 32:291 (1985), have discussed sequence-directed crosslinking ("complementary addressed modification") using an N-(2chloroethyl)-N-methylaniline group attached to either the 3'- or 5'-terminus of oligonucleotides. Summerton and Bartlett, *J. Mol. Biol.*, 122:145 (1978) have shown that an 8-atom chain, attached to a cytosine residue at its C-4 position and terminating in the highly reactive bromomethyl ketone group, can crosslink to the N-7 of guanosine. Webb and Matteucci, *Nucleic Acids Res.*, 14:7661 (1986), have prepared oligonucleotides containing a 5-methyl-N,N-ethanocytosine base which is capable of slow crosslinking with a complementary strand. In a conceptually related alkylation via a linker arm within a DNA hybrid, Iverson and Dervan, *Proc. Natl. Acad. Sci. USA*, 85:4615 (1988), have shown opposite strand methylation, triggered by BrCN activation of a methylthio ether, predominately on a guanine base located two pairs from the base bearing the linker. Vlassov et al. in *Gene* 72 (1988) 313–322, describe sequence specific binding and alkylation of plasmid DNA with oligodeoxynucleotide derivatives containing 2-chloroethyl-N-methyl amino phenyl residues. Similar cross-linking, using different cross-linking agent was described by Shaw et al., *J. Am. Chem. Soc.* 1991, 113, 7765–7766.

Further information pertaining to ODNs, chemically modified ODNs and their ability to affect or inhibit replication or translation of a target sequence of DNA or RNA can be found in European Patent Application No. 86309090.8, PCT publication WO8707611, U.S. Pat. No. 4,599,303, EP 0259186, PCT publication WO8503075, German Patent DE3310337, and in the publications Blake et al., *Biochemistry* 24:6139 (1985); Umlauf et al., "Triple-helical DNA Pairing Intermediates Formed by recA Protein,", *Biol. Chem.*, 265(28), 16898–16912 (1990); and Thuong et al., "Chemical synthesis of natural and modified oligodeoxynucleotides.", *Biochimie*, 1985, 67, 673–684.

DNA mapping

In addition to chemotherapy or potential chemotherapy utilizing ODNs or modified ODNs, a broad field has developed in the prior art for DNA mapping (gene mapping), that is, for in vitro determination of DNA sequence or partial DNA sequence. An important step in such DNA sequencing (gene mapping) is the cleavage of the target DNA into smaller fragments. The modified ODNs of the present invention also have utility in this field.

SUMMARY OF THE INVENTION (1) In one aspect the present invention relates to oligonucleotides (ODNs) which have at least one cross-linking agent covalently attached to the oligonucleotide, either to an internal or to a terminal nucleotide unit, and which have a base sequence sufficiently complementary to a single stranded target sequence so as to sequence specifically form a Watson-Crick bonded complex with the target sequence, and therafter covalently react with the target sequence. Such ODNs can be used for therapeutic purposes as anti-sense agents (targeting messenger RNA) or as sequence specific probes for diagnostic and analytical purposes.

(2) In a second aspect the present invention relates to ODNs which have at least two electrophilic cross linking agents covalently attached to the oligonucleotide, either to an internal or to a terminal nucleotide unit, and which are complementary in the Hoogsteen or reverse Hoogsteen pairing sense to a target sequence in double-stranded DNA. The two cross-linking agents may be attached to two different sites of the ODN. Alternatively, the cross-linking agent which is attached to one site on the ODN has two cross-linking functionalities, and therefore in effect comprises two cross-linking agents. The ODNs constructed in accordance with this aspect of the invention form a sequence specific (in the Hoogsteen or reverse Hoogsteen sense) triple stranded complex with the target sequence of double stranded DNA, and the cross-linking agents covalently react with nucleophilic sites on both strands of the target DNA sequence. ODNs in accordance with this aspect of the invention are useful as anti-gene (chemotherapeutic) agents targeting the DNA of an invading cell, organism or pathogen, such as a virus, fungus, parasite, bacterium or malignant cell. ODNs in accordance with this aspect of the invention are also useful as tools for DNA sequencing, gene mapping and related in vitro analytical and diagnostic procedures. Therefore, the target DNA may also be a gene or other duplex DNA which is to be sequenced ("mapped") or otherwise analyzed or investigated in vitro.

(3) In a third aspect, the present invention relates to ODNs which have in a substantially continuous sequence at least approximately 26 nucleotide units homologous to a target sequence in double stranded DNA. (Those skilled in the art will readily understand that the sequence of the ODN which is homologous to a target sequence of one strand of double stranded DNA is also complementary in the Watson Crick sense to the second strand of the same target sequence in the DNA.) The ODNs in accordance with this aspect of the invention have one or more electrophilic cross linking agents covalently attached to the oligonucleotide, either to an internal or to a terminal nucleotide unit. In vitro, and in the presence of a recombinase enzyme these ODNs are capable of forming sequence specific complexes with the target sequence of double stranded DNA based upon the full "four letter code" Watson Crick type recognition motif, and cross-link with at least one strand of the DNA. In vivo, due to the presence of recombinase enzyme in cells, the ODNs in accordance with this aspect of the invention also form complexes with the target sequence of double stranded DNA and cross-link with at least one strand of the target. In accordance with this aspect of the invention the cross-linking function is preferably attached to a nucleotide unit which is internal in the ODN.

The cross-linking function typically includes a linker arm (such as an alkyl, alkoxy, aminoalkyl or amidoalkyl chain) and an electrophilic reactive group which, after complexing with the target sequence of DNA or mRNA is capable of reacting with the target DNA to form a covalent bond therewith. As a result of the covalent bond formation between the modified ODN and the target sequence, replication and/or expression of the target sequence is inhibited, or in diagnostic or mapping application the target is "labeled", or a site for cleavage is created.

The ODNs of the present invention, in addition to having a covalently attached cross-linking agent, may also have other modifications, such as modifications of the heterocyclic bases, of the sugar as well as of the phosphate moieties, relative to naturally occurring ribonucleotides and deoxyribonucleotides. The cross-linking agents may be attached to either the heterocyclic bases, to the sugars or modified sugars, or to the phosphate or modified phosphate moieties.

DETAILED DESCRIPTION OF THE INVENTION

General Embodiments

As is known in the art, oligonucleotides (ODNs) comprise a chain of nucleotides which are linked to one another by phosphate ester linkages. Each nucleotide typically comprises a heterocyclic base (nucleic acid base), a sugar moiety attached to the heterocyclic base, and a phosphate moiety which esterifies a hydroxyl function of the sugar moiety. The principal naturally occurring nucleotides include uracil, or thymine, cytosine, adenine and guanine as the heterocyclic bases, and ribose or deoxyribose as the sugar moiety. The foregoing brief summary of basic nucleotide and oligonucleotide structural chemistry is mentioned because, in accordance with the broad principles of the present invention, at least one chemical cross-linking agent group is attached to an oligonucleotide which is complementary to a target sequence of RNA, single or double stranded DNA, as explained in detail below.

The oligonucleotides of the invention may comprise ribonucleotides (containing ribose as the only or principal sugar component), deoxyribonucleotides (containing deoxyribose as the principal sugar component), or in accordance with established state-of-the-art modified sugars or sugar analogs may be incorporated in the ODN of the present invention. Thus, in addition to ribose and deoxyribose, the sugar moiety may be pentose, deoxypentose, hexose, deoxyhexose, glucose, arabinose, xylose, lyxose, and a sugar "analog" cyclopentyl group. The sugar may be in a pyranosyl or in a furanosyl form. In the modified ODNs of the present invention the sugar moiety is preferably the furanoside of ribose, deoxyribose, arabinose, 2-fluoro-2-deoxyribose or 2-O-methylribose, and the sugar may be attached to the respective heterocyclic bases either in α or β anomeric configuration. The preparation of these sugars or sugar analogs and of the respective "nucleosides" wherein such sugars or analogs are attached to a heterocyclic base (nucleic acid base) per se is known, and need not be described here, except to the extent such preparation is provided here in connection with one or more specific examples. Preferably the sugar moiety is ribofuranose, 2-deoxyribofuranose or 2-fluoro-2-deoxyribofuranose in the β configuration.

The phosphorous derivative (or modified phosphate group) which may be attached to the sugar or sugar analog moiety in the modified oligonucleotides of the present invention may be a monophosphate, alkylphosphate, alkanephosphate, phosphorothioate, phosphorodithioate or the like. The preparation of the above-noted phosphate analogs, and their incorporation into nucleotides, modified nucleotides and ODNs, per se, is also known and need not be described here. Preferably, the phosphate derivative incorporated into the therapeutic oligonucleotides of the present invention is a "simple" phosphate, which in an internucleotidic bond forms a phosphate diester, and which at the 3' and 5' ends of the modified ODNs of the invention may carry the cross-linking agent. In this regard it is noted that recombinase enzymes recognize such "simple" phosphates and deoxyribose backbones. The cross-linking agent is described in substantial detail below.

The heterocyclic bases, or nucleic acid bases which are incorporated in the modified ODNs of the present invention may be the naturally occurring principal purine and pyrimidine bases, (namely uracil, or thymine, cytosine, adenine and guanine, as mentioned above), as well as naturally occurring and synthetic modifications of said principal bases. Those skilled in the art will recognize that a large number of "synthetic" non-natural nucleosides comprising various heterocyclic bases and various sugar moieties (and sugar analogs) have become available in the prior art, and that as long as other criteria of the present invention (such as being "complementary" to a target sequence of RNA or DNA, as applicable, in the Watson Crick, Hoogsteen or reverse Hoogsteen sense, as applicable) are satisfied, the novel ODNs of the invention may include one or several heterocyclic bases other than the principal five base components of naturally occurring nucleic acids. Preferably, however, the heterocyclic base in the modified ODNs of the present invention is selected from uracil-5-yl, cytosin-5-yl, adenin-2-yl, adenin-7-yl, adenin-8-yl, guanin-7-yl, guanin-8-yl, 4-aminopyrrolo[2,3d]pyrimidin-5-yl, 2-amino-4-oxopyrrolo[2,3-d]pyrimidin5-yl, 4-aminopyrazolo[3,4-d]pyrimidin-3-yl or 4-amino-6-oxopyrazolo[3,4-d]pyrimidin-3-yl groups, where the purines are attached to the sugar moiety of the oligonucleotides via the 9-position, the pyrimidines via the 1-position, the pyrrolopyrimidines via the 7-position and the pyrazolopyrimidines via the 1-position.

The cross-linking agents incorporated in the present invention need to meet the requirements that (1) each cross-linking agent must be covalently bonded to a site on the ODN, (2) its length and steric orientation must be such that it can reach a suitable reaction site in the target sequence after the ODN is hybridized or complexed with the target (with or without the assistance of an enzyme) (3) and must have a reactive group which will react with a reactive group of the target sequence. As noted above, the cross-linking agents may be covalently attached to the heterocyclic bases, to the sugar or modified sugar residues, or to the phosphate or modified phosphate functions of the ODNs. Any covalent attachment of the cross-linking agent to the ODN and any combination of covalent attachment of two or more cross-linking agents to the ODN is within the broad scope of the present invention.

In the simplest terms the cross-linking agent itself may conceptually be divided into two groups or moieties, namely the reactive group, which is typically and preferably an electrophilic leaving group (L), and an "arm" (A) which attaches the leaving group L to the respective site on the ODN. The leaving group L may be chosen from, for example, such groups as chloro, bromo, iodo, $SO_2R'''$, or $S^+R'''R''''$, where each of $R'''$ and $R''''$ is independently $C_{1-6}$alkyl or aryl or $R'''$ and $R''''$ together form a $C_{1-6}$alkylene bridge. Chloro, bromo and iodo are preferred. Within these groups haloacetyl groups such as $—COCH_2I$, and bifunctional "nitrogen mustards", such as $—N—[(CH_2)_2—Cl]_2$ are preferred. The leaving group will be altered by its leaving ability. Depending on the nature and reactivity of the particular leaving group, the group to be used is chosen in each case to give the desired specificity of the irreversibly binding probes.

Although as noted above the "arm" (or linker arm) A may conceptually be regarded as a single entity which covalently bonds the ODN to the leaving group L, and maintains the leaving group L at a desired distance and steric position relative to the ODN, in practice the "arm" A may be constructed in a synthetic scheme where a bifunctional molecule is covalently linked to the ODN (for example by a phosphate ester bond to the 3' or 5' terminus, or by a carbon-to-carbon bond to a heterocyclic base) through its first functionality, and is also covalently linked through its second functionality (for example an amine) to a "hydrocarbyl bridge" (alkyl bridge, alkylaryl bridge or aryl bridge, or the like) which, in turn, carries the leaving group.

A general formula of the cross linking function is thus $—A—L$, or $—A—L_2$ where L is the above defined leaving group and A is a moiety that is covalently linked to the ODN. The A "arm" moiety itself should be unreactive (other than through the leaving group L) under the conditions of hybridization of the ODN with the target DNA sequence, and should maintain the leaving group L in a desired steric position and distance from the desired site of reactions such as an N-7 position of a guanosine residue in the target sequence. Generally speaking, the length of the A group should be equivalent to the length of a normal alkyl chain of approximately 2 to 50 carbons.

An exemplary more specific formula for a class of preferred embodiments of the cross-linking function is $—(CH_2)_q—Y—(CH_2)_m—L$, where L is the leaving group, defined above, each of m and q is independently 0 to 8, inclusive, and where Y is defined as a "functional linking group". A "functional linking group" is a group that has two functionalities, for example $—NH_2$ and $—OH$, or $—COOH$ and $—OH$, or $—COOH$ and $—NH_2$, which are capable of linking the $(CH_2)_q$ and $(CH_2)_m$ bridges. An acetylenic terminus ($HC≡C—$) is also a suitable functionality as a precursor for Y, because it can be coupled to certain heterocycles and thereafter hydrogenated, as described below.

Other exemplary and more specific formulas for a class of preferred embodiments of the cross-linking function are $—(CH_2)_q—NH—CO—(CH_2)_m—(X)_n—N(R_1)—(CH_2)_p—L$ and $—(CH_2)_{q'}—O—(CH_2)_{q''}—NH—CO—(CH_2)_m—(X)_n—N(R_1)—(CH_2)_p—L$ where q, m and L are defined as above, q' is 3 to 7 inclusive, q'' is 1 to 7 inclusive, X is phenyl or simple substituted phenyl (such as chloro, bromo, lower alkyl or lower alkoxy substituted phenyl), n is 0 or 1, p is an integer from 1 to 6, and $R_1$ is H, lower alkyl or $(CH_2)_p—L$. Preferably p is 2. Those skilled in the art will recognize that the structure $—N(R_1)—(CH_2)_2—L$ describes a "nitrogen mustard", which is a class of potent alkylating agents. Particularly preferred within the scope of the present invention are those modified ODNs where the cross-linking agent includes the functionality $—N(R_1)—(CH_2)_2—L$ where L is halogen, preferably chlorine; and even more preferred are those modified ODNs where the cross linking agent includes the grouping $—N—[(CH_2)_2—L]_2$ (a "bifunctional" N—mustard).

A particularly preferred partial structure of the cross linking agent includes the grouping $—CO—(CH_2)_3—C_6H_4—N—[(CH_2)_2Cl]_2$.

In a particularly preferred embodiment the just-noted cross-linking group is attached to an n-hexylamine bearing tail at the 5' and 3' ends of the ODN in accordance with the following structure:

$R'—O—(CH_2)_6—NH—CO—(CH_2)_3—C_6H_4—N—[(CH_2)_2Cl]_2$ where R' signifies the terminal 5' or 3'-phosphate group of the ODN.

Other examples for the A—L group, particularly when attached to a heterocyclic base in the oligonucleotide (such as to the 5-position of 2'-deoxyuridine) are 3-iodoacetamidopropyl, 3-(4-bromobutyramido)propyl, 4-iodoacetamidobutyl and 4-(4-bromobutyramido)butyl groups.

In accordance with other preferred embodiments, the cross-linking functionality is covalently linked to the heterocyclic base, for example to the uracil moiety of a 2'-deoxyuridylic acid building block of the ODN. The linkage can occur through the intermediacy of an amino group, that is, the "arm-leaving group combination" (A—L) may be attached to a 5-amino-2'-deoxyuridylic acid building unit of the ODN. In still other preferred embodiments the "arm-leaving group combination" (A—L) is attached to the 5-position of the 2'-deoxyuridylic acid building unit of the ODN by a carbon-to-carbon bond. Generally speaking, 5substituted-2'-deoxyuridines can be obtained by an adaptation of the general procedure of Robins et al. (Can. J. Chem., 60:554 (1982); J. Org. Chem., 48:1854 (1983)), as shown in Reaction Scheme 1. In accordance with this adaptation, the palladium-mediated coupling of a substituted 1-alkyne to 5-iodo-2'-deoxyuridine gives an acetylene-coupled product. The acetylenic dUrd analog is reduced, with Raney nickel for example, to give the saturated compound, which is then used for direct conversion to a reagent for use on an automated DNA synthesizer, as described below. In Reaction Scheme 1,q is defined as above, and Y' is either Y (as defined above) or is a suitable protected derivative of Y. Y' can also be defined as a group which terminates in a suitably protected nucleophilic function, such as a protected amine. Examples of reagents which can be coupled to 5-iodo-2'-deoxyuridine in accordance with this scheme are $HC≡CCH_2OCH_2CH_2N(CO)_2C_6H_4$ (phtalimidoethoxypropyne), $HC≡CCH_2OCH_2CH_2NHCOCF_3$ (trifluoroacetamidoethoxypropyne), $HC≡CCH_2N(CO)_2C_6H_4$ (phtalimidopropyne) and $HC≡CCH_2NHCOCF_3$ (trifluoroacetamidopropyne).

In these examples the nucleosides which are obtained in this scheme are incorporated into the desired ODN, and the alkylating portion of the cross-linking agent is attached to the terminal amino group of "Y'" only after removal of the respective phtalic or trifluoroacetyl blocking groups.

Another particularly preferred example of an "arm-leaving group combination" (A—L) is attachment of a nitrogen-mustard type alkylating agent (or other alkylating agent) to the amino function of a 5-(3-aminopropyl)-2'-deoxyuridine building unit of the ODN. The appropriate nucleotide building unit for ODN synthesis which includes the 5-(3-aminopropyl)-2'-deoxyuridine nucleoside moiety can be obtained in analogy to Reaction Scheme 1, and in accordance with the teaching of Meyer et al., J. Am. Chem. Soc. 1989, 111, 8517. In this particularly preferred embodiment the nucleotide having the 5-(3-aminopropyl)-2'-deoxyuridine moiety is incorporated into the ODN by routine synthesis, and the cross-linking function is introduced by reacting the ODN with an activated form of a "nitrogen mustard", such as 2,3,5,6-tetrafluorophenyl- 4'-[bis(2-chloroethyl)amino]phenylbutyrate (Chlorambucil 2,3,5,6-tetrafluorophenyl ester; chlorambucil itself is commercially available).

examination of double-stranded DNA by ball-and-stick models and high resolution computer graphics indicates that the 7-position of the purines and the 5-position of the pyrimidines lie in the major groove of the B-form duplex of double-stranded nucleic acids. These positions can be substituted with side chains of considerable bulk without interfering with the hybridization properties of the bases. These side arms may be introduced either by derivatization of dThd or dCyd, or by straightforward total synthesis of the heterocyclic base, followed by glycosylation. These modified nucleosides may be converted into the appropriate activated nucleotides for incorporation into oligonucleotides with an automated DNA synthesizer. With the pyrazolo[3,4-d]pyrimidines, which are analogs of adenine, the crosslinking arm is attached at the 3-position, which is equivalent to the 7-position of purine.

The crosslinking side chain (arm=A) should be of sufficient length to reach across the major groove from a purine 7- or 8-position, pyrimidine 5-position, pyrrolopyrimidine 5-position or pyrazolopyrimidine 3-position and react with the N-7 of a purine (preferably guanine) located above (on the oligomer 3'-side) the base pair containing the modified analog. The crosslinking side chain (arm=A) holds the functional group away from the base when the base is paired with another within the double-stranded complex. As noted above, broadly the arm A should be equivalent in length to a normal alkyl chain of 2 to 50 carbons. Preferably, the arms include alkylene groups of 1 to 12 carbon atoms, alkenylene groups of 2 to 12 carbon atoms and 1 or 2 olefinic bonds, alkynylene groups of 2 to 12 carbon atoms and 1 or 2 acetylenic bonds, or such groups substituted at a terminal point with nucleophilic groups such as oxy, thio, amino or chemically blocked derivatives thereof (e.g., trifluoroacetamido, phthalimido, CONR', NR'CO, and $SO_2NR'$, where R'=H or $C_{1-6}$alkyl). Such functionalities, including aliphatic or aromatic amines, exhibit nucleophilic properties and are capable of serving as a point of attachment to such groups as —$(CH_2)_m$—L,
—CO—$(CH_2)_m$—$(X)_n$—$N(R_1)$—$(CH_2)_p$—L, and
—CO—$CH_2$—L which are described above as components of exemplary cross-linking functional groups.

After the nucleoside or nucleotide unit which carries the crosslinking functionality A—L, or a suitable precursor Reaction Scheme 1

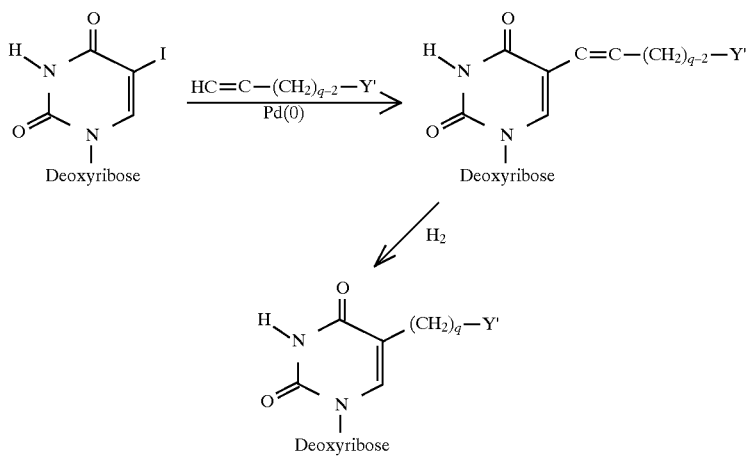

Reaction Scheme 1

Other examples of nucleotides where the crosslinking agent is attached to a heterocyclic base, are 2'-deoxy-4-aminopyrazolo[3,4-d]pyrimidine derivatives. The general structure of these derivatives is shown below in Formula 1. A—L represents the "arm" and the "leaving group" of the cross-linking functionality, as described above. $R_1$ represents the sugar moiety as described above, and $R_4$ and $R_6$ independently are H, OR, SR, NHOR, $NH_2$ or $NH(CH_2)_tNH_2$, where R is H or $C_{1-6}$alkyl, t is 0 to 12. These compounds can be made from 3,4-disubstituted and 3,4,6-trisubstituted pyrazolo[3,4-d]pyrimidines, in accordance with the teaching of Kobayashi in Chem. Phar. Bull. 21:941–951 (1973) which is incorporated herein by reference.

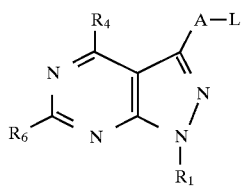

Formula 1

Discussing still in general terms the structures of the modified ODNs of the present invention, it is noted that thereof, (such as the —$(CH_2)_q$—$NH_2$ or —$(CH_2)_q$—Y group, where Y terminates with a nucleophilic group such as $NH_2$) is prepared, further preparation of the modified oligonucleotides of the present invention can proceed in accordance with state-of-the-art. Thus, to prepare oligonucleotides, protective groups are introduced onto the nucleosides or nucleotides and the compounds are activated for use in the synthesis of oligonucleotides. The conversion to protected, activated forms follows the procedures as described for 2'-deoxynucleosides in detail in several reviews. See, Sonveaux, *Bioorganic Chemistry*, 14:274–325 (1986); Jones, in "Oligonucleotide Synthesis, a Practical Approach", M. J. Gait, Ed., IRL Press, p. 23–34 (1984).

The activated nucleotides are incorporated into oligonucleotides in a manner analogous to that for DNA and RNA nucleotides, in that the correct nucleotides will be sequentially linked to form a chain of nucleotides which is complementary to a sequence of nucleotides in target DNA or RNA. The nucleotides may be incorporated either enzymatically or via chemical synthesis. The nucleotides may be converted to their 5'-O-dimethoxytrityl-3'-(N,N-diisopropyl) phosphoramidite cyanoethyl ester derivatives, and incorporated into synthetic oligonucleotides following the procedures in "Oligonucleotide Synthesis: A Practical Approach", supra. The N-protecting groups are then removed, along with the other oligonucleotide blocking groups, by post-synthesis aminolysis, by procedures generally known in the art.

In a preferred embodiment, the activated nucleotides may be used directly on an automated DNA synthesizer according to the procedures and instructions of the particular synthesizer employed. The oligonucleotides may be prepared on the synthesizer using the standard commercial phosphoramidite or H-phosphonate chemistries.

A moiety containing the leaving group, such as a haloacyl group (CO—$CH_2$—L where L is halogen for example I) or —CO—$(CH_2)_m$—$(X)_n$—$N(R_1)$—$(CH_2)_p$—L group (even more preferably a CO—$(CH_2)_3$—$C_6H_4$—N—$[CH_2CH_2Cl]_2$) may be added to the aminoalkyl or like groups (—$(CH_2)_q$—Y) following incorporation into oligonucleotides and removal of any blocking groups. For example, addition of an α-haloacetamide may be verified by a changed mobility of the modified compound on HPLC, corresponding to the removal of the positive charge of the amino group, and by subsequent readdition of a positive charge by reaction with 2-aminoethanethiol to give a derivative with reverse phase HPLC mobility similar to the original aminoalkyl-oligonucleotide.

In the situations where the cross linking agent (A—L moiety) is attached to the 3' or 5' terminus of the oligonucleotide, for example by an alkylamine linkage of the formula —$(CH_2)_q$—Y (Y terminating in an amine), the oligonucleotide synthesis may be performed to first yield the oligonucleotide with said aminoalkyl tail, to which then an alkylating moiety, such as the above-noted haloacylgroup (CO—$CH_2$—L) or —CO—$(CH_2)_m$—$(X)_n$—$N(R_1)$—$(CH_2)_p$—L is introduced.

Generally speaking the oligonucleotides of the invention may include up to approximately 3000 nucleotide units, although shorter oligonucleotides are preferred, as described below.

CROSS-LINKING OLIGONUCLEOTIDES FOR ANTI-SENSE THERAPY AND APPLICATION AS PROBES FOR SINGLE STRANDED DNA AND RNA

In accordance with the first broad aspect of the invention the ODN of the invention is used to hybridize with and cross-link with single stranded RNA, such as mesenger RNA, or single stranded DNA. Duplex formation and cross-linking with messenger RNA can serve therapeutic purposes (anti-sense) in that by incapacitating the messenger RNA it inhibits gene expression resulting in protein synthesis. Hybridization and cross linking in an in vitro system can serve for diagnostic and analytical purposes. In each instance of utilization of the ODNs in accordance with this aspect of the invention, the ODN has a nucleotide sequence which is complementary (or substantially complementary) in the Watson Crick sense to the target sequence in the single stranded RNA or single stranded DNA, and at least one covalently attached cross-linking agent. Further description of utilizing the ODNs of the present invention as hybridization probes and evidence of sequence specific cross-linking to single stranded DNA (fragments of human papilloma virus (HPV) and human cytomegalovirus (HCV) sequence) and related experimental details are given below.

Probes may be labeled by any one of several methods typically used in the art. A common method of detection is the use of autoradiography with $^3H$, $^{125}I$, $^{35}S$, $^{14}C$, or $^{32}P$ labeled probes or the like. Other reporter groups include ligands which bind to antibodies labeled with fluorophores, chemiluminescent agents, and enzymes. Alternatively, probes can be conjugated directly with labels such as fluorophores, chemiluminescent agents, enzymes and enzyme substrates. Alternatively, the same components may be indirectly bonded through a ligand-antiligand complex, such as antibodies reactive with a ligand conjugated with label. The choice of label depends on sensitivity required, ease of conjugation with the probe, stability requirements, and available instrumentation.

The choice of label dictates the manner in which the label is incorporated into the probe. Radioactive probes are typically made using commercially available nucleotides containing the desired radioactive isotope. The radioactive nucleotides can be incorporated into probes, for example, by using DNA synthesizers, by nick-translation, by tailing of radioactive bases in the 3' end of probes with terminal transferase, by copying M13 plasmids having specific inserts with the Klenow fragment of DNA polymerase in the presence of radioactive dNTP's, or by transcribing RNA from templates using RNA polymerase in the presence of radioactive rNTP's.

Non-radioactive probes can be labeled directly with a signal (e.g., fluorophore, chemiluminescent agent or enzyme) or labeled indirectly by conjugation with a ligand. For example, a ligand molecule is covalently bound to the probe. This ligand then binds to a receptor molecule which is either inherently detectable or covalently bound to a detectable signal, such as an enzyme or photoreactive compound. Ligands and antiligands may be varied widely. Where a ligand has a natural "antiligand", namely ligands such as biotin, thyroxine, and cortisol, it can be used in conjunction with its labeled, naturally occurring antiligand. Alternatively, any haptenic or antigenic compound can be used in combination with a suitably labeled antibody. A preferred labeling method utilizes biotin-labeled analogs of oligonucleotides, as disclosed in Langer et al., *Proc. Natl. Acad. Sci. USA* 78:6633–6637 (1981), which is incorporated herein by reference.

Enzymes of interest as reporter groups will primarily be hydrolases, particularly phosphatases, esterases, ureases and glycosidases, or oxidoreductases, particularly peroxidases. Fluorescent compounds include fluorescein and its derivatives, rhodamine and its derivatives, dansyl, umbelliferone, rare earths, etc. Chemiluminescers include luciferin, acridinium esters and 2,3-dihydrophthalazinediones, e.g., luminol.

The specific hybridization conditions are not critical and will vary in accordance with the investigator's preferences and needs. Various hybridization solutions may be employed, comprising from about 20% to about 60% volume, preferably about 30%, of a polar organic solvent. A common hybridization solution employs about 30–60% v/v formamide, about 0.5 to 1M sodium chloride, about 0.05 to 0.1M buffers, such as sodium citrate, Tris HCl, PIPES or HEPES, about 0.05% to 0.5% detergent, such as sodium dodecylsulfate, and between 1–10 mM EDTA, 0.01% to 5% ficoll (about 300–500 kdal), 0.1% to 5% polyvinyl-pyrrolidone (about 250–500 kdal), and 0.01% to 10% bovine serum albumin. Also included in the typical hybridization solution will be unlabeled carrier nucleic acids from about 0.1 to 5 mg/ml, e.g., partially fragmented calf thymus or salmon sperm DNA, and/or partially fragmented yeast RNA and optionally from about 0.5% to 2% wt./vol. glycine. Other additives may also be included, such as volume exclusion agents which include a variety of polar water-soluble or swellable agents, such as anionic polyacrylate or polymethylacrylate, and charged saccharidic polymers, such as dextran sulfate.

The particular hybridization technique is not essential to the invention. Hybridization techniques are generally described in "Nucleic Acid Hybridization, A Practical Approach", Hames and Higgins, Eds., IRL Press, 1985; Gall and Pardue, *Proc. Natl. Acad. Sci., U.S.A.*, 63:378–383 (1969); and John et al., *Nature*, 223:582–587 (1969). As improvements are made in hybridization techniques, they can readily be applied.

The amount of labeled probe which is present in the hybridization solution may vary widely. Generally, substantial excess of probe over the stoichiometric amount of the target nucleic acid will be employed to enhance the rate of binding of the probe to the target DNA or RNA.

Various degrees of stringency of hybridization can be employed. As the conditions for hybridization become more stringent, there must be a greater degree of complementarity between the probe and the target for the formation of a stable duplex. The degree of stringency can be controlled by temperature, ionic strength, the inclusion of polar organic solvents, and the like. For example, temperatures employed will normally be in the range of about 20° to 80° C., usually 25° to 75° C. For probes of 15–50 nucleotides in 50% formamide, the optimal temperature range can vary from 22°–65° C. With routine experimentation, one can define conditions which permit satisfactory hybridization at room temperature. The stringency of hybridization is also conveniently varied by changing the ionic strength and polarity of the reactant solution through manipulation of the concentration of formamide within the range of about 20% to about 50%.

Treatment with ultrasound by immersion of the reaction vessel into commercially available sonication baths can oftentimes accelerate the hybridization rates.

After hybridization at a temperature and time period appropriate for the particular hybridization solution used, the glass, plastic, or filter support to which the probe-target hybrid is attached is introduced into a wash solution typically containing similar reagents (e.g., sodium chloride, buffers, organic solvents and detergent), as provided in the hybridization solution. These reagents may be at similar concentrations as the hybridization medium, but often they are at lower concentrations when more stringent washing conditions are desired. The time period for which the support is maintained in the wash solutions may vary from minutes to several hours or more.

Either the hybridization or the wash medium can be stringent. After appropriate stringent washing, the correct hybridization complex may now be detected in accordance with the nature of the label.

The probe may be conjugated directly with the label. For example, where the label is radioactive, the support surface with associated hybridization complex substrate is exposed to X-ray film. Where the label is fluorescent, the sample is detected by first irradiating it with light of a particular wavelength. The sample absorbs this light and then emits light of a different wavelength which is picked up by a detector ("Physical Biochemistry", Freifelder, D., W. H. Freeman & Co., 1982, pp. 537–542). Where the label is an enzyme, the sample is detected by incubation with an appropriate substrate for the enzyme. The signal generated may be a colored precipitate, a colored or fluorescent soluble material, or photons generated by bioluminescence or chemiluminescence. The preferred label for dipstick assays generates a colored precipitate to indicate a positive reading. For example, alkaline phosphatase will dephosphorylate indoxyl phosphate which then will participate in a reduction reaction to convert tetrazolium salts to highly colored and insoluble formazans.

Detection of a hybridization complex may require the binding of a signal generating complex to a duplex of target and probe polynucleotides or nucleic acids. Typically, such binding occurs through ligand and antiligand interactions as between a ligand-conjugated probe and an antiligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label. (Tijssen, P., "Practice and Theory of Enzyme Immunoassays, Laboratory Techniques in Bio-chemistry and Molecular Biology", Burdon, R. H., van Knippenberg, P. H., Eds., Elsevier, 1985, pp. 9–20).

The amount of labeled probe present in the hybridization solution may vary widely, depending upon the nature of the label, the amount of the labeled probe that can reasonably bind to the cellular target nucleic acids, and the precise stringency of the hybridization medium and/or wash medium. Generally, substantial probe excesses over the stoichiometric amount of the target will be employed to enhance the rate of binding of the probe to the target nucleic acids.

This first aspect of the invention is also directed to a method or identifying target single stranded nucleic acid sequences, which method comprises utilizing an oligonucleotide probe including at least one ODN having a cross-linking agent and a label as described above.

In one embodiment, the method comprises the steps of:
(a) denaturing nucleic acids in the sample to be tested;
(b) hybridizing to the target nucleic acids an oligonucleotide probe (hereinafter sometimes "probe") including at least one labeled ODN having a cross-linker covalently attached, wherein the ODN comprises a sequence complementary to that of the target nucleic acid sequence;
(c) washing the sample to remove unbound probe;

(d) incubating the sample with detecting agents; and (e) inspecting the sample.

The above method may be conducted following procedures well known in the art.

An assay for identifying target single stranded nucleic acid sequences utilizing a labeled oligonucleotide probe including the covalently attached cross-linking agent and comprising the above method is contemplated for carrying out the invention. Such an assay may be provided in kit form. For example, a typical kit includes the probe reagent (ODN) having a sequence complementary to that of the target nucleic acids; a denaturation reagent for converting double-stranded nucleic acid to a single-stranded nucleic acid; and a hybridization reaction mixture. The kit can also include a signal-generating system, such as an enzyme for example, and a substrate for the system.

The following examples are provided to illustrate the present invention without limiting same. "RT" means room temperature.

General

Thin layer chromatography was performed on silica gel 60 F 254 plates (Analtech) using the following solvent mixtures: A—90% methylene chloride:10% methanol; B—50% ethyl acetate: 50% hexanes; C—70% ethyl acetate: 10% methanol: 10% water: 10% acetone; D—50% ether: 50% hexanes. Flash chromatography was performed using 60 F 254 silica (Merck). Oligonucleotides were synthesized on an Applied Biosystems Model 380B Synthesizer. oligonucleotides were isotopically labeled using T4 Polynucleotide kinase (BRL) and $\tau\text{-}^{32}\text{P-ATP}$ (New England Nuclear).

EXAMPLE 1

6-(Tritylamino)caproic Acid

6-Aminocaproic acid (26 g, 0.2 mole) was dissolved in dichloromethane (200 mL) by the addition of triethylamine (100 mL). Trityl chloride (120 g, 0.45 mole) was added and the solution stirred for 36 hours. The resulting solution was extracted with 1N HCl and the organic layer evaporated to dryness. The residue was suspended in 2-propanol/1N NaOH (300 mL/100 mL) and refluxed for 3 hours. The solution was evaporated to a thick syrup and added to dichloromethane (500 mL). Water was added and acidified. The phases were separated, and the organic layer dried over sodium sulfate and evaporated to dryness. The residue was suspended in hot 2-propanol, cooled, and filtered to give 43.5 (58%) of 6-(tritylamino)caproic acid, useful as an intermediate compound.

EXAMPLE 2

5-(Tritylamino) pentylhydroxymethylenemalononitrile

To a dichloromethane solution of 6-(tritylamino)caproic acid (20.0 g, 53 mmole) and triethylamine (20 mL) in an ice bath was added dropwise over 30 min isobutylchloroformate (8.3 mL, 64 mmole). After the mixture was stirred for 2 hours in an ice bath, freshly distilled malononitrile (4.2 g, 64 mmole) was added all at once. The solution was stirred for 2 hours in an ice bath and for 2 hours at RT. The dichloromethane solution was washed with ice cold 2N HCl (300 mL) and the biphasic mixture was filtered to remove product that precipitated (13.2 g). The phases were separated and the organic layer dried and evaporated to a thick syrup. The syrup was covered with dichloromethane and on standing deposited fine crystals of product. The crystals were filtered and dried to give 6.3 g for a total yield of 19.5 g (87%) of the product, which is useful as an intermediate.

EXAMPLE 3

5-(Tritylamino) pentylmethoxymethylenemalononitrile

A suspension of the malononitrile of Example 2 (13 g, 31 mmole) in ether/dichloromethane (900 mL/100 mL), cooled in an ice bath, was treated with a freshly prepared ethereal solution of diazomethane (from 50 mmole of Diazald$^R$ (Aldrich Chemical Company)). The solution was stirred for 6 hours and then neutralized with acetic acid (10 mL). The solution was evaporated to dryness and the residue chromatographed on silica gel using dichloromethane/acetone (4/1) as the eluent. Fractions containing product were pooled and evaporated to a syrup. The syrup was triturated with dichloromethane to induce crystallization. The crystals were filtered an dried to give 8.3 g (61%) of chromatographically pure product, useful as an intermediate compound.

EXAMPLE 4

5-Amino-3-[(5-tritylamino)pentyl]pyrazole-4-carbonitrile

To a methanol solution (100 mL) of the product of Example 3 (7.0 g, 16 mmole) in an ice bath was added hydrazine monohydrate (7.8 mL, 160 mmole) dropwise over 15 min. After stirring for 30 min in an ice bath, the solution was evaporated to dryness. The residue was suspended in cold methanol and filtered to give 7.1 g (100%) of 5-amino-3-[(5-tritylamino)pentyl]pyrazole-4carbonitrile, useful as an intermediate, after drying. An analytical sample was prepared by recrystallization from water.

EXAMPLE 5

5-Amino-1-(2-deoxy-3, 5-di-O-toluoyl-β-D-erythropentofuranosyl)-3-[(5-tritylamino)pentyl] pyrazole-4-carbonitrile An ice cold solution of the carbonitrile from Example 4 (3.5 g, 8 mmole) was treated with sodium hydride and stirred for 30 min at 0°–4° C. 1-Chloro-1,2dideoxy-3,5-di-O-toluoylribofuranose was added and the solution stirred for 1 hour at 0°–4° C. The solution was poured into a saturated solution of sodium bicarbonate and extracted with dichloromethane. The organic layer was dried over sodium sulfate and evaporated to dryness. The residue was flash chromatographed. The organic layer was dried over sodium sulfate and evaporated to dryness. The residue was flash chromatographed on silica gel using toluene/ethyl acetate (5/1) as eluent. Two major products were isolated and identified as the N-1 and N-2 isomers in 57% (3.6 g) and 20% (1.2 g) N-1 and N-2 yields, respectively. Approximately 1 g of a mixture of N-1 and N-2 isomers was also collected. Overall yield of glycosylated material was 5.8 g (92%). The N-1 isomer, 5-amino-1-(2-deoxy-3,5-di-o-toluoyl-β-D-erythropentofuranosyl)-3-[(5-tritylamino)-pentyl]pyrazole-4-carbonitrile, was used without further purification in Example 6.

EXAMPLE 6

1-(2-Deoxy-β-D-erythropentofuranosyl)-3-[5-(tritylamino)-pentyl]pyrazolo[3,4-d]pyrimidin-4-amine To a toluene (100 mL) solution of the pyrazole-4-carbonitrile of Example 5 (3.5 g, 4.4 mmole) was added diethoxymethyl acetate (1.1 mL, 6.7 mmole). The solution was kept at 80°–90° C. for 5 hours and then evaporated to a syrup. The syrup was dissolved in dichloromthane (10 mL) and added to ice cold methanolic ammonia (100 mL) in a glass pressure bottle. After two days at RT the contents of the bottle were evaporated to dryness. The residue was dissolved in methanol and adjusted to pH 8 with freshly prepared sodium methoxide to complete the deprotection. After stirring overnight the solution was treated with Dowex$^R$-50 H+ resin, filtered and evaporated to dryness. The residue was chromatographed on silica gel using acetone/hexane (3/2) as eluent to give 2.0 g (77%) of analytically pure product.

EXAMPLE 7

1-(2-Deoxy-β-D-erythropentofuranosyl)-3-[5-(tritylamino)-pentyl]pyrazolo[3,4-d]pyrimidin-4-amine 5'-monophosphate To an ice cold solution of the pyrazolopyrimidin-4-amine of Example 6 (250 mg, 0.43 mmole) in trimethyl phosphate (5 mL) was added phosphoryl chloride (50 μL) and the solution was kept at 0°–4° C. The reaction was monitored by reversed phase HPLC using a linear gradient from 0 to 100% acetonitrile in water over 25 min. After stirring for 5 hours, an additional aliquot of phosphoryl chloride (25 μL) was added and the solution was stirred another 30 min. The solution was poured into 0.1M ammonium bicarbonate and kept in the cold overnight. The solution was then extracted with ether and the aqueous layer evaporated to dryness. The residue was dissolved in water (5 mL) and purified by reversed phase HPLC using a 22 mm×50 cm C18 column. The column was equilibrated in water and eluted with a gradient of 0 to 100% acetonitrile over 20 min. Fractions containing the desired material were pooled and lyophilized to give 160 mg (56%) of chromatographically pure nucleotide.

EXAMPLE 8

1-(2-Deoxy-β-D-erythropentofuranosyl)-3-{5-[(6-biotinamido)hexanamido]pentyl}pyrazolo[3,4-d]pyrimidin-4-amine 5'-monophosphate An ethanol solution (10 mL) of the nucleotide of Example 7, palladium hydroxide on carbon (50 mg), and cyclohexadiene (1 mL) was refluxed for 3 days, filtered, and evaporated to dryness. The residue was washed with dichloromethane, dissolved in DMF (1.5 mL) containing triethylamine (100 mL), and treated with N-hydroxysuccinimidyl biotinylaminocaproate (50 mg). After stirring overnight an additional amount of N-hydroxysuccinimidyl 6-biotinamidocaproate (50 mg) was added and the solution was stirred for 18 hours. The reaction mixture was evaporated to dryness and chromatographed following the procedure in Example 7. Fractions were pooled and lyophilized to give 80 mg of chromatographically pure biotinamido-substituted nucleotide.

EXAMPLE 9

1-(2-Deoxy-β-D-erythroventofuranosyl)-3-[5-(6-biotinamido)-hexanamidopentyl]pyrazolo[3,4-d]pyrimidin-4-amine 5'-triphosphate The monophosphate of Example 8 (80 mg, ca. 0.1 mmole) was dissolved in DMF with the addition of triethylamine (14 μL). Carbonyldiimidazole (81 mg, 0.5 mmole) was added and the solution stirred at RT for 18 hours. The solution was treated with methanol (40 μL), and after stirring for 30 minutes tributylammonium pyrophosphate (0.5 g in 0.5 mL DMF) was added. After stirring for 24 hours another aliquot of tributylammonium pyrophosphate was added and the solution was stirred overnight. The reaction mixture was evaporated to dryness and chromatographed following the procedure in Example 8. Two products were collected and were each separately treated with conc. ammonium hydroxide (1 mL) for 18 hours at 55° C. UV and HPLC analysis indicated that both products were identical after ammonia treatment and were pooled and lyophilized to give 35.2 mg of nucleoside triphosphate.

EXAMPLE 10

NICK-TRANSLATION REACTION

The triphosphate of Example 9 was incorporated into pHPV-16 using the nick translation protocol of Langer et al. (supra). The probe prepared with the triphosphate of Example 9 was compared with probe prepared using commercially available bio-11-dUTP (Sigma Chemical Co). No significant differences could be observed in both a filter hybridization and in situ smears.

More specifically, the procedure involved the following materials and steps

Materials:
    DNase (ICN Biomedicals)—4 μg/mL
    DNA polymerase 1 (U.S. Biochemicals)—8 U/mL
    PHPV—16—2.16 mg/mL which is a plasmid containing the genomic sequence of human papillomavirus type 16.
    10X-DP—1M Tris, pH7.5(20 mL); 0.5M OTT(80 mL); 1M MgCl$_2$(2.8 mL); H$_2$O (17 mL)
    Nucleotides—Mix A—2 mM each dGTP, dCTP, TTP (Pharmacia)
    Mix U—2 mM each dGTP, DcTP, dATP
    Bio-11-dUTP—1.0 mg/mL (BRL)
    Bio-12-dAPPTP—1.0 mg/mL Steps:
To an ice cold mixture of 10X-DP (4 mL), pHV-16 (2 mL), nucleotide mix A (6 mL), Bio-12-dAPPTP (2 mL), and H$_2$O (20 mL) was added DNase (1 mL) and DNA polymerase 1 (2.4 mL). The reaction mixture was incubated at 16° C. for 1 hour. The procedure was repeated using Bio-11dUTP and nucleotide mix U in place of Bio-12-dAPPTP (comprising the triphosphate of Example 9) and nucleotide mix A.

Nucleic acid was isolated by ethanol precipitation and hybridized to pHPV-16 slotted onto nitrocellulose. The hybridized biotinylated probe was visualized by a streptavidin-alkaline phosphatase conjugate with BCIP/NBT substrate. Probe prepared using either biotinylated nucleotide gave identical signals. The probes were also tested in an in situ format on cervial smears and showed no qualitative differences in signal and background.

EXAMPLE 11

5-Amino-3-[(5-tritylamino)pentyl]pyrazole-4-carboxamide

Following the procedure of Example 2, except that cyanoacetamide is used instead of malononitrile, 5-(tritylamino)pentylhydroxymethylececyanoacetamide is prepared from 6-(tritylamino)caproic acid. This is then treated with diazomethane to give the methoxy derivative, following the procedures of Example 3, which is then reacted with hydrazine monohydrate, as in Example 4, to give 5-amino-3-[(5-tritylamino)pentyl]pyrazole-4-carboxamide.

EXAMPLE 12

4-Hydroxy-6-methylthio-3-[(5-tritylamino)pentyl] pyrazolo-[3,4-d]pyrimidine

The carboxamide from Example 11 is reacted with potassium ethyl xanthate and ethanol at an elevated temperature to give the potassium salt of 4-hydroxypyrazolo[3,4-d] pyrimidine-6-thiol. This salt is then reacted with iodomethane to give 4-hydroxy-6methylthio-3-[(5-tritylamino)pentyl]pyrazolo[3,4-d]pyrimidine.

EXAMPLE 13

1-(2-Deoxy-β-D-erythropentofuranosyl)-4-hydroxy-3-[5-(tritylamino)pentyl]pyrazolo[3,4-d]pyrimidin-6-amine Following the procedure of Example 5, the pyrazolopyrimidine of Example 12 is treated with sodium hydride and reacted with 1-chloro-1,2-dideoxy-3,5-di-O-toluoylribofuranose. The resulting compound is reacted with MCPBA and with methanolic ammonia, and the toluoyl protecting groups are removed to give the product.

EXAMPLE 14

1-(2-Deoxy-β-D-erythropentofuranosyl)-4-hydroxy-3-[5-(6-biotinamido)hexanamidopentyl]pyrazolo[3,4-d]pyrimidin-6-amine 5'-monophosphate Following the procedure of Example 7, the pyrazolopyrimidine of Example 13 is reacted with phosphoryl chloride to give the corresponding 5'-monophosphate.

Following the procedure of Example 8, the above 5'-monophosphate is reacted with palladium/carbon and cyclohexadiene, and the residue is reacted with N-hydroxysuccinimidyl biotinylaminocaproate to give 1-(2-deoxy-β-D-erythropentofuranosyl)-4-hydroxy-3-[5-(6-biotinamido) hexanamidopentyl]pyrazolo[3,4-d]pyrimidin-6-amine 5'-monophosphate.

EXAMPLE 15

1-(2-Deoxy-β-D-erythropentofuranosyl)-4-hydroxy-3-[5-(6-biotinamido)hexanamidopentyl]pyrazolo[3, 4-d]pyrimidin-6-amine 5'-triphosphate Following the procedure of Example 9, the 5'-monophosphate of Example 14 is treated with carbonyldiimidazole and then reacted with tributylammonium pyrophosphate to give the corresponding 5'-triphosphate.

EXAMPLE 16

1-(2-Deoxy-β-D-erythropentofuranosyl)-3-[5-(tritylamino)-pentyl]pyrazolo[3,4-d]pyrimidine-4-benzoylamine 1-(2-Deoxy-β-D-erythropentofuranosyl)-3-[5-(tritylamino)pentyl]pyrazolo[3,4-d]pyrimidine-4-amine from Example 6 is reacted with benzoyl chloride and pyridine to give 1-(2-deoxy-3,5-di-O-benzoyl-β-D-erythropentofuranosyl)-3-[5-(tritylamino)pentyl]pyrazolo-[3,4-d]-pyrimidine-4-dibenzoylamine. This is treated with aqueous sodium hydroxide to partially deprotect the compound giving 1(2-deoxy-β-D-erythropentofuranosyl)-3-[5-(tritylamino)pentyl]pyrazolo[3,4-d]pyrimidine-4benzoylamine.

EXAMPLE 17

1-(2-Deoxy-β-D-erythropentofuranosyl)-3-[5-(trifluoroacetamido)pentyl]pyrazolo[3,4-d] pyrimidine-4-benzoylamine Following the procedure of Example 8, the benzoylamine of Example 16 is treated with palladium hydroxide on carbon and then with trifluoroacetic anhydride to give 1-(2-deoxy-β-D-erythropentofuranosyl)-3-[5-(trifluoroacetamido)pentyl]pyrazolo[3,4-d]pyrimidine-4-benzoylamine.

EXAMPLE 18

1-(2-Deoxy-5-O-dimethoxytrityl-β-D-erythropentofuranosyl)-3-[5-(trifluoroacetamido) pentyl]pyrazolo[3,4-d]pyrimidine-4-benzoylamine 3'-O-(N,N-diisopropyl)phosphoramidite cyanoethyl ester The compound of Example 17 is reacted with dimethoxytrityl chloride and pyridine to give the corresponding 5'-dimethoxytrityl compound. This compound is then reacted with cyanoethyl chloro-N,N-diisopropylphosphoramidite (according to the method of Sinha et al., *Nucleic Acids Res.*, 12:4539 (1984)) to give the 3'-O-activated nucleoside.

EXAMPLE 19

5-(4-Phthalimidobut-1-yn-1-yl)-2'-deoxyuridine

5-Iodo-2'-deoxyuridine (354 mg, 1 mmol) was dissolved in 10 mL of dimethylformamide. Cuprous iodide (76 mg, 0.4 mmol), tetrakis(triphenylphosphine)palladium(0) (230 mg, 0.2 mmol), and triethylamine (200 mg, 2.0 mmol) were added. 4-Phthalimidobut-1-yne (300 mg, 1.5 mmol) was added all at once and the reaction kept at 60° C. for three hours. The clear yellow reaction was then evaporated and methylene chloride was added. Scratching of the flask induced crystallization of nearly all of the product which was filtered and recrystallized from 95% ethanol to give 335 mg (78%) of title compound as fine, feathery needles.

EXAMPLE 20

5-(4-Phthalimidobut-1-yl)-2'-deoxyuridine 1.00 Gram of 5-(4-Phthalimidobut-1-yn-1-yl)-2'-deoxyuridine was dissolved in 95% EtOH and about 3 g of neutral Raney nickel was added. After 48 hours, the catalyst was removed by cautious filtration and the filtrate was evaporated to a solid which was recrystallized from methanol-water to give 960 mg (97%) of the title compound.

EXAMPLE 21

5-(3-Iodoacetamidopropyl)-2'-deoxyuridine 5-(3-Trifluoroacetamidoprop-1-yl)-2'-deoxyuridine (0.3 mmol) is treated with ammonia and then with N-hydroxysuccinimidyl α-iodoacetate (0.5 mmol). The reaction mixture is evaporated to dryness and purified by chromatography to give 5-(3-iodoacetamidopropyl)-2'-deoxyuridine.

EXAMPLE 22

5-(4-(4-Bromobutyramido)butyl)-2'-deoxyuridine 5-(4-phthalimidobut-1-yl)-2'-deoxyuridine is treated with ammonia and then with N-hydroxysuccinimidyl-4-bromobutyrate to give 5-(4-(4-bromobutyramido)butyl)-2'-deoxyuridine.

Preparation of Synthetic Oligonucleotides

EXAMPLE 23

Phosphoramidite Preparation and DNA Synthesis

Nucleosides were 5'-dimethoxytritylated, following known procedures, to give around 85% yield, and the 3'-phosphoramidite was made using diisopropylamino β-cyanoethylchlorophosphite (as described in "Oligonucleotide Synthesis: A Practical Approach", supra) with diisopropylethylamine in methylene chloride. The phosphoramidite was made into a 0.2N solution in acetonitrile and placed on the automated DNA synthesizer. Incorporation of these new and modified phosphoramidites gave incorporation similar to ordinary phosphoramidites (97–99% as judged by assay of the trityl color released by UV.)

oligonucleotides were removed from the DNA synthesizer in tritylated form and deblocked using 30% ammonia at 55° C. for 6 hours. Ten µL of 0.5M sodium bicarbonate was added to prevent acidification during concentration. The oligonucleotide was evaporated to dryness under vacuum and redissolved in 1.0 mL water. The oligonucleotides were purified by HPLC using 15–55% acetonitrile in 0.1N triethylammonium acetate over 20 minutes. Unsubstituted oligonucleotides came off at 10 minutes; amino derivatives took 11–12 minutes. The desired oligonucleotide was collected and evaporated to dryness, then it was redissolved in 80% aqueous acetic acid for 90 minutes to remove the trityl group. Desalting was accomplished with a G25 Sephadex column and appropriate fractions were taken. The fractions were concentrated, brought to a specific volume, dilution reading taken to ascertain overall yield and an analytical HPLC done to assure purity. Oligonucleotides were frozen at −20° C. until use.

Following the above procedures, the nucleoside 5-(3-trifluoroacetamidoprop-1-yl)-2'-deoxyuridine was converted to the 5'-O-dimethoxytrityl-3'-(N,N-diisopropyl)-phosphoramidite cyanoethyl ester derivative. This was added to a DNA synthesizer and the following 14-mer oligonucleotide sequence was prepared:
SEQ ID NO:1 3'-CT TCC U$^1$TG TAG GTC-5'
where U$^1$ is 5-(3-aminoprop-1-yl)-2'-deoxyuridine (oligo A).

In the same manner, 5-(4-phthalimidobut-1-yl)-2'-deoxyuridine was converted to the 5'-(O-dimethoxytrityl-3'-(N,N-diisopropyl)phosphoramidite cyanoethyl ester derivative and added to a DNA synthesizer to prepare the above 14-mer oligonucleotide sequence where U$^1$ is 5-(4-aminobut-1-yl)-2'-deoxyuridine (oligo C).

A corresponding 14-mer oligonucleotide was also prepared where U$^1$ is the unmodified deoxyuridine.

EXAMPLE 24

Derivatization of Oligonucleotides

In general, to add the crosslinking arm to an aminoalkyloligonucleotide, a solution of 10 µg of the aminoalkyloligonucleotide and a 100× molar excess of n-hydroxysuccinimide haloacylate such as α-haloacetate or 4-halobutyrate in 10 µL of 0.1M borate buffer, pH 8.5, was incubated at ambient temperature for 30 min. in the dark. The entire reaction was passed over a NAP-10 column equilibrated with and eluted with distilled water. Appropriate fractions based on UV absorbance were combined and the concentration was determined spectrophotometrically.

Introduction of the haloacyl moiety was examined by HPLC. A Zorbax$^R$ oligonucleotide column (Dupont) eluted with a 20 minute gradient of 60% to 80% B composed of: A (20% acetonitrile:80% 0.02N NaH$_2$PO$_4$) and B (1.2N NaCl in 20% acetonitrile:80% 0.02N NaH$_2$PO$_4$). The presence of a reactive a-haloacyl moiety was indicated by return of the retention time of the α-haloacylamidoalkyl oligonucleotide to the corresponding aminoalkyl oligonucleotide after exposure to 1N cysteamine. Introduction of cysteamine created equivalent charge patterns between the aminoalkyl oligonucleotide and the α-haloacylamido oligonucleotide.

Following the above procedure, the 14-mer oligonucleotide:
SEQ ID NO:1 3'-CT TCC U$^1$TG TAG GTC-5'
where U$^1$ is 5-(3-aminoprop-1-yl)-2'-deoxyuridine (oligo A, Example 23), was reacted with n-hydroxysuccinimide α-iodoacetate to give the above 14-mer oligonucleotide where U$^1$ is 5-(3-iodoacetamidoprop-1-yl)-2'-deoxyuridine (oligo B).

Oligo A and oligo B, as well as the above 14-mer where U$^1$ is the unmodified deoxyuridine were resolved in the Zorbax column, all of identical sequence, with the following retention times: unmodified 14-mer, 9.31 min; aminopropyl 14-mer (oligo A), 7.36 min; and iodoacetamido-propyl 14-mer (oligo B), 10.09 min.

In the same manner, the aminopropyl 14-mer (oligo A) was reacted with N-hydroxysuccinimide 4-bromobutyrate to give the 14-mer where U$^1$ is 5-(3-(4-bromobutyramido) prop-1-yl)-2'-deoxyuridine.

Also, the aminobutyl 14-mer (oligo C, Example 23) was reacted with either N-hydroxysuccinimide α-iodoacetate or N-hydroxysuccinimide 4-bromobutyrate to give the 14-mer where U$^1$ is 5-(4-iodoacetamidobut-1-yl)-2-deoxyuridine or 5-(4-(4-bromobutyramido)but-1-yl)-2'-deoxyuridine, respectively.

Assays

EXAMPLE 25

Assay of Crosslinking Reaction to Single Stranded DNA

The reaction of crosslinking a DNA probe to a target nucleic acid sequence contained 1 µg of haloacylamidoalkyl probe and 10 ng of $^{32}$P-labeled cordycepin-tailed target in 200 µL of 0.1M Tris, pH 8.0, and 0.9M NaCl incubated at 20° or 30° C. Aliquots were removed at 24- or 72-hour intervals and diluted in 20 µL of 10 mM cysteamine to quench the haloacylamido group. These solutions were stored at RT, and 1 µL was used for analysis by denaturing polyacrylamide gel electrophoresis (PAGE).

Following the above procedure, two model oligonucleotide sequences were utilized to evaluate the crosslinkage potential of the modified probe to its complement. The sequences, derived from human papillomavirus (HPV) or human cytomegalovirus (CMV), are shown below:

HPV System:

```
                          5         10        15        20        25        30
SEQ ID NO:1  Target:  5'-AGA  CAG  CAC  AGA  ATT  CGA  AGG  AAC  ATC  CAG-3'
SEQ ID NO:2  Probe:                              3'-CT  TCC  UTG  TAG  GTC-5'
```

CMV System:

```
                          5         10        15        20
SEQ ID NO:3  Target:  5'-ACC  GTC  CTT  GAC  ACG  ATG  GAC  TCC-3'
SEQ ID NO:4  Probe:                  3'-GAA  CTG  TGC  UAC  CTC-5'
```

U = 5-[3-(α-iodoacetamido)- or 3-(4-bromobutyr-
    amido)-propyl-2'-deoxyuridine, or
U = 5-[3-(α-iodoacetamido)- or 4-(4-bromobutyr-
    amido)-butyl]-2'-deoxyuridine.

The target for HPV is a 30-mer, and for CMV it is a 24-mer. The crosslinking probes were a 14-mer for HPV and two 15-mers for CMV. Each probe contained a single modified deoxyuridine designated as U in the sequences above.

The reaction of HPV target with a limiting amount of crosslinking probe containing a 5-(3-iodoacetamidopropyl) sidearm can be analyzed in a cleavage pattern on a denaturing PAGE gel, and the analysis showed the loss of the crosslinked hybrid with the concomitant appearance of a discrete low molecular weight band. The intensity of this band was dependent upon the extent of crosslinkage in the initial reaction. The localization of signal into two discrete bands on the gel strongly argues that no non-sequence-directed alkylation of either target or probe strands had occurred (including intramolecular probe alkylation).

Comparison with an authentic 15-mer run in an adjacent lane suggested that the major cleaved fragment is a 9-mer. Upon close examination of the original autoradiogram, a slower moving band of very weak intensity was visible. This pattern would be consistent with major alkylation at G-21 and minor alkylation at G-20. An examination of a Dreiding model of the crosslinkable HPV hybrid shows that the 5-(3-iodoacetamidopropyl) sidearm can contact the G-21 residue of the target strand with only minor distortion of the helix.

If alkylation occurs predominately at a guanosine on the target strand located two units on the 5' side of the modified-deoxyuridine base pair, the CMV sequence should not react. This result was in fact observed. The absence of reaction with CMV further supports the specificity of the crosslinking scheme of the invention.

EXAMPLE 26

Time and Temperature Dependence

Time and temperature dependence studies were carried out with the HPV system of Example 25 where U is 5-(3-iodoacetamidoprop-1-yl)-2'-deoxyuridine. The target was $^{32}$P-labeled by cordycepin tailing with terminal transferase (Maniatis et al., "Molecular Cloning—A Laboratory Manual", Cold Spring Harbor Laboratory, 1982, p. 239) and incubated with excess probe in a pH 8.0 Tris buffer at either 20° or 30° C. Aliquots were removed after 0, 24, or 72 hours incubation, quenched with an equivalent volume of 10 mM mercaptoethylamine (which reacts with the iodoacetamide), and stored at RT for subsequent analysis by denaturing or non-denaturing PAGE.

Crosslinkage of the hybrid, which was monitored by denaturing PAGE, was evident for the 24 and 72 hour time points at both temperatures. The amount of crosslinked hybrid increased with both temperature and time. Approximately 20% of the hybrid was crosslinked after 72 hours incubation at 30° C.

Separate experiments at a range of temperatures indicated that the half-life for crosslinking at 37° C. is approximately 2 days, and that the reaction is complete after 24 hours at 58° C. This time-dependent reaction implies that the iodoacetamido moiety does not hydrolyze or react with the buffer. The increased reaction rate at higher temperature indicates that the hybrid is maintained, and subsequently the rate of alkylation shows the expected increase with temperature.

EXAMPLE 27

Site Specificity of Alkylation

To elucidate the site specificity of alkylation, the crosslinked HPV hybrid of Example 25 (where U is 5-(3-iodoacetamidoprop-1-yl)-2'-deoxyuridine) was subjected to a 10% piperidine solution at 90° C. for 60 minutes. As shown by Maxam et al. (*Proc. Natl. Acad. Sci. USA* 74:560 (1977), this treatment quantitatively cleaves the target strand 3'-to the site of alkylation. The resulting data indicated that the alkylation of the second guanine above the crosslinker-modified base pair (i.e., the quanine above the target base) was the exclusive reaction observed, indicating that the crosslinking reaction in the HPV model system is remarkably specific.

CROSS-LINKING OLIGONUCLEOTIDES HAVING TWO CROSS-LINKING FUNCTIONS FOR ANTI-GENE THERAPY AND APPLICATION AS PROBES FOR DOUBLE STRANDED DNA AND DNA MAPPING

In accordance with the second broad aspect of the invention the ODN has at least two covalently attached crosslinking agents. The ODN in this aspect of the invention preferably has no more than approximatley 300, and preferably no more than approximately 60 nucleotide units. The cross linking agents may be attached at the 3' or 5' phosphate terminus, or to the sugar or any heterocyclic base within the ODN. A cross-linking agent which has two cross-linking functionalities, such as a crosslinking agent having the formula —N—[(CH$_2$)$_2$—L]$_2$ (a bifunctional N-mustard) is capable of two alkylations, and is therefore considered as two cross-linking agents in this aspect of the invention. The ODN bearing the two cross-linking agents in accordance with this aspect of the invention is complementary in the Hoogsteen or reverse Hoogsteen pairing sense to the target double stranded DNA. There is evidence in accordance with this aspect of the invention that when the ODN has one covalently attached bifunctional cross linking agent (bifunctional N-mustard) then after triplex formation the modified ODN attaches to both strands of the target double stranded DNA sequence. Alternatively, cross-linking agents are attached to at least two different sites of the ODN. In this case also, evidence indicates that two separate covalent bonds are formed with the target DNA sequence. In both situations, in accordance with this aspect of the invention, formation of at least two covalent bonds with the target DNA is attained.

As noted above, the modified ODN of the present invention forms a triplex with the target double stranded DNA sequence. This is followed by cross-linkage which inactivates the target DNA sequence. Following triple strand formation and covalent crosslinkage, the modified target DNA no longer supports replication or transcription. Unlike all other lesions in DNA, however, this modification is much less likely to be repaired by the organism. Normally, cross-linked DNA is repaired by a combination of excision repair and homologous recombination. With cross-linked triple strand complexes, however, there will be no undamaged copies of the targeted gene to participate in recombination. By analogy with procaryotic models, the eucaryotic cell may attempt to use a misrepair (or SOS) pathway wherein the crosslink will be removed, but at the expense of mutagenesis. In such case, gene function is likely to be irreversibly silenced by the resultant mutations.

The use of recombination enzymes in combination with anti-gene ODNs significantly enhances the efficiency with which the single strand ODN "finds" its complementary target DNA sequence. Accordingly, the efficiency of triple strand formation is greatly increased when the anti-gene ODN is combined with a recombination enzyme (for instance, in a nucleoprotein complex).

Within the present invention, suitable target DNA sequences include deleterious structural genes and both associated up-stream and down-stream regulatory control sequences so that their deactivation brings about a therapeutically beneficial result. Target sequences also include genes of invading organisms, such as viral, fungi, parasites, bacteria and tumor cells. The regulatory sequences may be involved in either transcription or replication. The anti-gene ODN is determined and designed according to the target DNA sequence chosen for alteration of function, and has a sequence complementary in the Hoogsteen or reverse Hoogsteen sense to a homoquine run in one of the two strands of the chosen target DNA.

In a particularly preferred embodiment, an antigene ODN is administered to a cell or a host, and upon entry to a target cell nucleus, the anti-gene ODN combines with recombination enzymes present within the nucleus. In this mode the ODN can bind to any complementary sequence of choice. In this mode the ODN can bind to any complementary sequence of choice. In an alternative embodiment, the anti-gene ODN and recombination enzyme are combined ex vivo and then administered to a cell or a host as a nucleoprotein filament. In this embodiment, it may be advantageous to administer the nucleoprotein filament in a liposome. Preferred recombination enzymes include procaryotic and eucaryotic recombination enzymes, such as recA, human recombinase and Drosophila recombinase, with human recombinase particularly preferred.

As it was noted above, experimental evidence proves that both of the minimum two cross-linking agents incorporated into the modified ODNs of the present invention actually react with the target DNA sequence, and that both strands of the target sequence are subsequently covalently linked and should be deactivated by the modified ODN.

Another important use or application of the modified ODNs of the present invention is in the field of mapping large DNA molecules, and related analytical and investigative techniques in the fields of molecular biology, genetics and biochemistry. For example, the ability to chemically restrict or cleave long double-stranded DNA at unique sites 10–20 base pairs in length has been frequently discussed as a technique which could accelerate the human genome project by providing a means for physically mapping large DNA molecules. In accordance with this aspect of the present invention a triple-stranded complex is allowed to form between a synthetic oligonucleotide (ODN) and a "complementary" 10–20 base long homopurine run in double-stranded DNA. Since the modified ODN of the present invention is appropriately appended with two alkylating agents, crosslinkage to two guanine residues on opposite strands of the duplex takes place. Crosslinks to guanine residues are known in the art to render the alkylated DNA susceptible to cleavage, for example through cleavage of the glycosidic bond between the alkylated guanine base and the sugar moiety, followed by cleavage of the phosphosdiester bond. The overall cleavage of the alkylated DNA at the alkylation sites may occur spontaneously, or as a result of an appropriate enzyme or other reagent acting on the modified DNA. In accordance with the presently preferred mode of this aspect of the invention the alkylated duplex DNA is incubated with an amino acid, lysine, arginine or histidine, or with a DNA associating protein (such as a histone or a recombinase enzyme). This converts each alkylation site into a cleavage site probably through the process of depurination (cleavage of glycosidic bond of the alkylated guanine residue) followed by beta elimination reaction.

More specifically, still in connection with the use of the modified ODNs of the present invention for "DNA mapping" or "gene mapping" or related investigative procedures, the following is noted. The structure of the modified ODN used in the process is known in accordance with the present invention. Thus, the modified ODN can be tailor made to cleave at one or more specific approximately 10 to 20 base pair regions (target regions) of the target DNA. The structure of the target region may be known already, in which case the modified ODN is created specifically for the target region pursuant to the rules of Hoogsteen or reverse Hoogsteen pairing. Alternatively, no specific site in the target DNA may be known, in which case the site of cleavage brought about as a result of hybridization with a modified ODN of known sequence nevertheless provides information about the existence and number of "matching" regions in the target DNA.

Thus, in accordance with this aspect of the invention and examples, a double-stranded plasmid DNA which contains a 20 base pair long homopurine/homopyrimidine run is chemically restricted. To effect cleavage 1–10 $\mu$g of the plasmid is incubated with 1–10 $\mu$M of a $C^+$/T, G/A or G/T motif 20 mer ODN designed to form a sequence specific triple strand with the homopurine run using the Hoogsteen or reverse Hoogsteen base pairing rules. (For an A rich homopurine run a $C^+$/T or G/A motif ODN is employed; for a G rich homopurine run a G/A or G/T motif ODN is used.) Triplexing is carried out overnight at 15°–37° C. in the presence of 10 mM $MgCl_2$ at pH 6.0 ($C^+$/T motif) or pH 7.0–7.5 (G/A or G/T motif). The $C^+$ symbol in the $C^+$/T motif stands for the 5-methylcytosine base which is better suited for Hoogsteen or reverse Hoogsteen pairing than cytosine.

The modified ODN which becomes the third strand during the incubation may have the two alkylating groups appended to either internal base residues or to the 5' or 3 ' terminus. Each alkylating group reacts with the N-7 position of a nearby guanine residue of the targeted duplex. Double stranded break of the duplex occurs because the two guanine residues reside on opposite strands of the duplex. In the case where the alkylating group is attached to an internal base on the third strand ODN, that base is purposely designed to form a mismatch with the opposing G—C or C—G base pair in the targeted duplex. This allows access to the N-7 position of guanine by the alkylator. By contrast, when the alkylating group is attached to the end of the ODN so as to target a guanine residue in the flanking duplex, the terminal base in the ODN is designed to hydrogen bond to the opposing base pair of the target. The general rules for placement of alkylating groups on the ODNs are illustrated by the three examples below where the upper strand is the crosslinkable third strand ODN; X represents a terminal alkylating group while Y represents an alkylating group attached to an internal 5-(3-aminopropyl)-2'-deoxyuridine residue. The guanine bases crosslinked in the target duplex are bold faced and underlined. The crosslinkable ODN is identified by a Sequence No. and the double stranded target, is also identified by a single Sequence No. Example 1 G/A motif ODN targeted to the homopurine run in human HLA DQB1 0302 allele:

SEQ ID NO:5

3'-XGAGAGAGGAAAGAGGAGAX

5'-ATATAAGGAGAGAGGAAAGAGGAGACAAA

SEQ ID NO:6

3'-TATATTCCTCTCTCCTTTCTCCTCTGTTT

Example 2 G/T motif ODN targeted to the homopurine run in human epidermal growth factor receptor:

SEQ ID NO:7

3'-GGGTGGTGYTGTGYTGGTGGTGTT

5'-GGGAGGAGCAGAGGAGGAGGAGAA

SEQ ID NO:8

3'-CCCTCCTCGTCTCCTCCTCCTCTT

Example 3 C+/T/G motif ODN targeted to a homopurine run in HIV proviral DNA:

SEQ ID NO:9

5'-TTTTCTTTTYGGGGGTX

5'-TTTTTAAAAGAAAAGGGGGGACTGG

SEQ ID NO:10

3'-AAAAATTTTCTTTTCCCCCCTGACC

After complexing the modified ODN to the target duplex and cross-linking the crosslinked DNA is incubated 12–24 hr at 37° with 10 mM lysine, arginine or histidine. As noted above, as a result of this procedure each crosslink is converted into a nick through a depurination and beta-elimination pathway. If the alkylated guanines are within 5–6 base pairs of one another the staggered nicks break the DNA; otherwise, breakage is be accomplished by brief incubation with exonuclease III (3' to 5' digestion) or calf spleen phosphodiesterase (5' to 3' digestion) to remove a portion of the intervening duplex. The choice of exonuclease depends upon the polarity of the target strands in relation to the positions of the nicks. If necessary, prior to exonuclease treatment the triplex can be destroyed by complexing magnesium ion with excess EDTA and then spinning the sample through a disposable gel filtration cartridge. The spin simultaneously removes the ODN and exchanges the plasmid into exonuclease buffer. After digestion the samples can be phenol extracted and alcohol precipitated for use in later experiments.

Specific Embodiments and Experimental Procedures 2,3, 5,6-Tetrafluorophenyl trifluoroacetate.

A mixture of 2,3,5,6-tetrafluorophenol (55.2 g, 0.33 mol), trifluoroacetic anhydride (60 mL, 0.42 mol) and boron trifluoride etherate (0.5 mL) was refluxed for 16 hr. Trifluoroacetic anhydride and trifluoroacetic acid were removed by distillation at atmospheric pressure. The trifluoroacetic anhydride fraction (bp 40° C.) was returned to the reaction mixture along with 0.5 mL of boron trifluoride etherate, and the mixture was refluxed for 24 hr. This process was repeated two times to ensure complete reaction. After distillation at atmospheric pressure, the desired product was collected at 62° C./45 mm (45° C./18 mm) as a colorless liquid: yield=81.3 g (93%); d=1.52 g/mL; $n_D^{21}$=1.3747; IR (CHCl$_3$) 3010, 1815, 1525, 1485, 1235, 1180, 1110, and 955 cm$^{-1}$. Anal. Calcd for $C_8HF_7O_2$: C, 36.66; H, 0.38; F, 50.74. Found: C, 36.31; H, 0.43; F, 50.95.

2,3,5,6-Tetrafluorophenyl-4'-[bis(2-chloroethyl)amino] phenylbutyrate (Chlorambucil 2,3,5,6-tetrafluorophenyl ester)

To a solution of 0.25 g (0.82 mmol) of chlorambucil (supplied by Fluka A. G.) and 0.3 g (1.1 mmol) of 2,3,5,6-tetrafluorophenyl trifluoroacetate in 5 ml of dry dichloromethane was added 0.2 Ml of dry triethylamine. The mixture was stirred under argon at room temperature for 0.5 h and evaporated. The residual oil was purified by column chromatography on silica gel with hexane-chloroform (2:1) as the eluting solvent to give the ester as an oil: 0.28 g (75%); TLC on silica gel (CHCl$_3$) R$_f$ 0.6; IR (in CHCl$_3$) 3010, 1780, 1613, 1521, 1485 cm$^{-1}$.

2-Proparqyloxvethyl)amine (John, R., and Seitz, G., Chem. Ber., 123, 133 (1990) was prepared by condensing propynol with 2-bromoethylammonlum bromide in liquid ammonia in the presence of Na NH$_2$, and was used crude for the next reaction.

3-(2-Trifluoroacetamidoethoxy)propyne (2-Propargyloxyethyl)amine (13.8 g, 0.14 mol) is stirred and chilled in an iso-propanol-dry ice bath while excess of trifluoroacetic anhydride (26 ml, 0.18 mol) is added dropwise. N-(2-Propargyloxyethyl)trifluoroacetamide is distilled at 84°–85 °/1.7 torr as an oil which solidified upon refrigeration; yield 14.4 g (52%), m.p. (16°, $n_p^{24}$ 1.4110. Anal. Calcd. for $C_7H_8F_3NO_2$: C, 43.09, H, 4.13; N, 7.18; F, 29.21. Found: C, 42.80; H, 4.03; N, 7.06; F, 29.38.

5-[3-(2-Trifluoroacetamidoethoxy)propynyl]-2'-deoxyuridine

A mixture of 5-iodo-2'-deoxyuridine (3.54 g, 10 mmol), copper(1) iodide (0.19 g, 1 mmol) and tetrakis (triphenylphosphine)palladium(O) (0.58 g, 0.5 mmol) is dried in vacuo at 60° for 3 hours and placed under argon. A suspension of the mixture in dry DMF (20 ml) is stirred under argon and treated with dry triethylamine (1.7 ml, 12 mmol) followed by 3-(2-Trifluoroacetamidoethoxy)propyne (3.17 g, 16 mmol). The mixture is cooled at room temperature in a water bath and stirred for 17 hours. The mixture is treated with 2% acetic acid (100 ml), the catalyst is removed by filtration and washed with 50% methanol. The filtrates are combined and passed onto a LiChroprep RP-18 column (5×25 cm), the column is washed, then eluted with 1% acetic acid in 50% (v/v) methanol. The fractions with the main product are combined, evaporated, and dried in vacuo. The resultant foam is stirred with 150 ml of ether to give crystalline product; yield 3.6 g (85%); m.p. 145°–152°.

5-[3-(2-Trifluoroacetamidoethoxy)propyl]12'-deoxyuridine

A solution of 5-[3-(2-trifluoroacetamidoethoxy)propynyl]-2'-deoxyuridine (3.4 g, 8.1 mmol) in methanol (20 ml) is stirred with ammonium formate (prepared by addition of 3 ml, 79 mmol of cold 98% formic acid into 2 ml, 50 mmol of dry ice frozen 25% ammonia) and 0.2 g of 10% Pd/C for 7 hours at room temperature under hydrogen atmosphere. The catalyst is removed by filtration, the filtrate evaporated and product is purified on LiChroprep RP-18 column by the above procedure. Fractions containing the desired product are combined and evaporated to dryness in vacuo and the resultant solid is triturated with dry ether to give 3.0 g (87% product, m.p. 107°–110°; $\lambda_{max}$ in nm, in 0.1M triethylamine-acetate (pH 7.5), 220, 268. Analysis calculated for $C_{16}H_{22}F_3N_3O_7$: C, 45.18; H, 5.21; N, 9.88; F, 13.40. Found C, 45.16; H, 5.16; N, 9.68; F, 13.13.

Preparation of Synthetic Oligonucleotides

Introduction of chlorambucil residue into the primary amino groups of oligonucleotides Preparation of the cetyltrimethylammonium salt of oligonucleotides: a 100 μL aliquot of aqueous solution of oligonucleotide (50–500 ug), generally triethylammonium salt, was injected to a column packed with Dowex 50wx8 in the cetyltrimethylammonium form and prewashed with 50% alcohol in water. The column was eluted by 50% aqueous ethanol (0.1 mL/min). Oligonucleotide containing fraction was dried on a Speedvac over 2 hours and used in following reactions.

Ethanol solution (50 uL) of cetyltrimethylammonium salt of an oligonucleotide (50–100 μg) was mixed with 0.08M solution of 2,3,5,6-tetrafluorophenyl-4'-[bis(2-chloroethyl)amino]phenylbutyrate (tetrafluorophenyl ester of chlorambucil) in acetonitrile (50 μL) and 3 μL of diisopropylethylamine. After shaking for three hours at room temperature, the product was precipitated by 2% $LiClO_4$ in acetone (1.5 mL). The product was reprecipitated from water (60 uL) by 2% $LiClO_4$ in acetone three times. Finally the chlorambucil derivative of the oligonucleotide was purified by Reverse Phase Chromatography with approximately 50–80% yield. The fraction containing the product was concentrated by addition of butanol. The isolated chlorambucil derivative of the oligonucleotide was precipitated in acetone solution with $LiClO_4$, washed by acetone and dried under vacuum. All manipulations of reactive oligonucleotide were performed as quickly as possible, with the product in ice-cold solution.

Demonstration of crosslinking of the third-strand oligonucleotide to both strands of a duplex DNA target within a triplex The following sequences were used to demonstrate bifunctional crosslinking:
SEQ ID NO:11 C: 5'-XCTTTCCTCTCTTTTCCCCX-3'
A: 5'-AAATACTGGGAGAAAGGAGAGAAAAGGGGA CCCAACGTAT-3'
SEQ ID NO:12 B: 3'-TTTATGACCCTCTTTCCTCTC TTTTCCCCTGGGTTGCATA-5'

The strands A and B form the Watson-Crick duplex by conventional base pairing, and C is the third strand, which pairs to strand A within the duplex by Hoogsteen or reverse Hoogsteen hydrogen bonding. The X residues in strand C bear the alkylating moiety which is shown by the formulas below. In this example, the p-[bis(2-chloroethyl)amino]phenylbutyrate group (designated CA) is bound to, in one case, a 5-(aminoethoxypropyl)deoxyuridine, which is the terminal nucleotide at either the 3'- or 5'-end, or at both ends, of the oligonucleotide C. In the second case, the alkylating group (CA) is bound to an aminohexyl group esterified to a phosphate at either the 3'- or 5'-end, or to both ends, of the oligonucleotide. The alkylating residue CA is placed onto the reactive amino group of the oligonucleotide by the method described above. Oligonucleotides were 5'-labeled with [Γ-$^{32}$P]ATP from DuPont (NEN Research Products; Boston, Mass.) and T4 polynucleotide kinase from United States Biochemical (Cleveland, Ohio) using the procedure of Maxam and Gilbert (Maxam, A. M.; Gilbert, W. (1980) Methods in Enzymology, 65, 499). The $^{32}$P-labeled product was purified using a Dupont Nensorb™ 20 column (Wilmington, Del.). Cerenkov counting was done on a Beckman LS 5000TD from Beckman Instruments, Inc. (Fullerton, Calif.). Oligonucleotide concentrations were calculated from $A_{260}$ values.

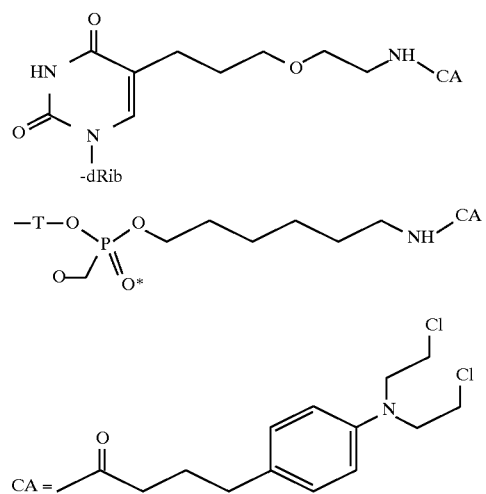

Each hybridization mixture contained 5 μL of the labelled oligonucleotide in water, conc 5×10$^{-7}$M, was mixed with 10 μL of complementary unlabelled strand, at the same conc, and with 5 μL of a buffer which contained 350 mM NaCl, 100 mM $MgCl_2$, and 125 mM Na cacodylate, pH 6.0. After mixing, the mixture was incubated at 37° for 1 hr, and then 5 μL of a solution of reactive oligonucleotide (which had been kept ice-cold until this time), conc 5×10$^{-5}$, was added, and incubation was continued at 37° for various times. Electrophoresis shows the formation of the slower moving bands that correspond to all three strands in the system being covalently linked together, indicating bifunctional crosslinking.

The position of cleavage was ascertained by treatment of the incubation mixtures with 1M pyrrolidine in water for 15 min, 2× evaporation from water, and then polyacrylamide gel electrophoresis on a 20% gel. This analysis showed specific cleavage of the labeled target strand at the expected site; specifically, the guanines immediately 5' to the strand C binding site on both strands A and B, which are indicated in the formula of the strands by underlining.

CROSS-LINKING OLIGONUCLEOTIDES HAVING A CROSS-LINKING FUNCTION FOR ANTI-GENE THERAPY AND APPLICATION AS PROBES FOR DOUBLE STRANDED DNA, WITH A SEQUENCE HOMOLOGOUS TO ONE STRAND OF THE TARGET DNA

In accordance with a third aspect of the present invention an ODN has at least one covalently attached cross-linking function and at least approximately 26 nucleotide units in a continuous sequence which are homologous to a target sequence in one strand of double stranded DNA (dsDNA). The ODN in this aspect of the invention has no more than approximately 3000 nucleotide units, preferably no more than approximately 300, and still more preferably no more than approximately 60.

Broadly speaking the cross-linking function is of the structure described above, namely it is an A—L or A—$L_2$ function, covalently attached either to an internal nucleotide unit or to a terminal nucleotide unit of the ODN. The nature of the A—L and A—$L_2$ function, the meaning of the A and L symbols and specific embodiments of these functions have been described above in connection with the first and second main embodiments or aspects of the invention. Presently preferred embodiments of the cross-linking function for crosslinking with double stranded DNA in accordance with this aspect of the invention include the α-haloacyl function as the reactive group, and the N-mustard type reactive group. Even more preferably the N-mustard type reactive group is attached to a 5-(3-aminopropyl) (or like) substituted 2'-deoxyuridine unit of the ODN. The N-mustard type reactive group is preferably a bis (2-chloroethyl)amine, more preferably derived from chlorambucil, and therefore has the structure CO—$(CH_2)_3$—$C_6H_4$—N—$[CH_2CH_2Cl]_2$). As noted above this "chlorambucil" moiety can be attached to the amino group of 5-(3-aminopropyl) (or like) substituted 2'-deoxyuridine unit of the ODN by reacting the ODN with 2,3,5,6-tetrafluorophenyl-4'-[bis(2-chloroethyl)amino]phenylbutyrate. Alternatively, in another preferred embodiment the cross-linking function is covalently attached to the 5' or 3'-end of the ODN through an alkylamine, preferably a hexylamine tail, as shown by the partial structure below.

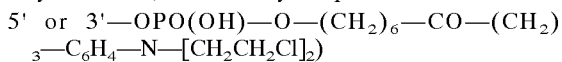

Preferably, the cross-linking function is covalently attached to a nucleotide unit which is internal on the ODN.

Sequence specific binding of the ODN to a double stranded DNA or DNA fragment and cross-linking to one DNA strand occurs in accordance with this aspect of the invention based on a "4-letter" Watson-Crick type recognition motif. It has been found however that in vitro a recombinase enzyme is needed for the binding and cross-linking to occur. The recombinase enzyme promotes binding of the ODN to the dsDNA as a triplex. In vivo, recombinase enzymes are virtually ubiquitous and the ODNs in accordance with this aspect of the invention undergo triplex formation and resultant cross-linking due to the presence of the indigenous recombinase enzyme in the cell. The invention however is not limited by the specific nature or origin of the recombinase enzyme, recombinases from single cell organisms as well as from cells of human or mammalian origin are capable of functioning within the invention. Because binding and cross-linking of the ODN to double stranded DNA occurs on the basis of the full "4-letter" Watson Crick recognition motif, this aspect of the invention provides a still broader basis for therapeutic application and as a sequence specific probe (for example for gene mapping) of double stranded DNA than the previously described aspect of the invention wherein the binding of the ODN to the dsDNA is based on Hoogsteen or reverse Hoogsteen pairing.

Since the action of a recombinase enzyme is necessary in accordance with this aspect of the invention, the ODNs designed in accordance with this aspect include sugar moieties in their nucleotide units which are compatible with recognition by the recombinase enzyme. Preferably the ODNs in accordance with this aspect comprise 2'-deoxyribonucleotides and their isosteric equivalents, 2'-O-alkyl ribonucleotides (alkyl of $C_1$–$C_6$ carbons) and 2'-deoxy-2-fluororibonucleotides.

As in the previously described aspect of the invention, target sequences of dsDNA can be deleterious structural genes and associated up-stream and downstream regulatory control sequences the deactivation of which brings about a therapeutically beneficial result. Target sequences also include genes of invading organisms, such as viruses, fungi, parasites, bacteria and tumor cells. The regulatory sequences may be involved in either transcription or replication. The anti-gene ODN of the invention is determined and designed according to the target DNA sequence chosen for alteration of function. The ODN has a sequence which is homolgous (or substantially homologous) to the target sequence in one of the two strands of the chosen target DNA. It follows from the foregoing that the sequence of the ODN which is "homologous" to one strand of the dsDNA or fragment thereof, is complementary in the Watson Crick sense to the other strand of the dsDNA, or fragment thereof. ODNs of this embodiment or aspect of the invention can be used for diagnostic, analytical, "gene-mapping" and like purposes substantially as described above for the second embodiment or aspect of the invention. The advantage of this embodiment is that it operates in a "four-letter" Watson Crick recognition mode.

It is an important feature or discovery in accordance with this aspect of the invention that the entire ODN does not need to be homologous (or complementary) to the dsDNA or fragment thereof, but there must be at least approximately 26, and preferably at least approximately 30 nucleotide units in a continuous sequence in the ODN which are homologous (or substantially homologous) to the matching sequence of the dsDNA (or fragment thereof). Moreover, the cross-linking function must be within or attached to an end of the continuous sequence of approximately 26, or more, homologous (or substantially homologous) nucleotide units.

The ability of the ODNs in accordance with the present invention to bind to dsDNA (or fragment therof) and cross-link therewith, provided the above-noted conditions are met, is demonstrated by the following experimental examples.

Experimental Examples of Cross-linking ODNs to Double Stranded DNA

In Vitro Examples

Materials and Methods

RecA protein was purchased from US Biochemical Corporation (Cleveland, Ohio). The restriction enzymes EcoRI, ScaI, PvuI and AseI were purchased from New England Biolabs (Beverly, Mass.). Proteinase K was obtained from Boeringer Mannheim Biochemicals (Indianapolis, Ind.).

Short dsDNA fragments (amplicons) 197 and 272 bp long were synthesized by standard PCR protocol (Perkin Elmer Cetus, Norwalk, Conn.) using EcoRI linearized pBR322 plasmid DNA (Promega) as a template. One of the primers for the amplification reaction was chemically phosphorylated during its synthesis to permit selective 5'-$^{32}$P-end labeling (using T4 Polynucleotide Kinase and [Γ-$^{32}$P]ATP) of only one strand of the dsDNA product. As a long dsDNA target pGEM-4Z plasmid DNA (Promega) was used after linearization with ScaI restriction endonuclease and subsequent 5'-$^{32}$P-end labeling of both strands. All 5'-$^{32}$P-end labeled dsDNA substrates were purified by non-denaturing PAGE or agarose gel electrophoresis prior to use to avoid any possible exonuclease or ssDNA contamination.

Oligonucleotides were synthesized by standard phosphoroamidite chemistry on an Applied Biosystems 394 DNA/RNA Synthesizer and purified by reverse phase HPLC. The chlorambucil reactive moiety was attached to 5-(3-aminopropyl)-2'-deoxyuridine residues in the oligonucleotides or to a 5'-aminohexyl phosphate group by postsynthetic acylation with chlorambucil 2,3,5,6-tetrafluorophenyl ester as described elsewhere above and in the article by Igor V. Kutyavin, Howard B. Gamper, Alexander A. Gall, and Rich B. Mayer, Jr. (1993) *J. Amer. Chem. Soc.* 115, 9303, which is incorporated herein by reference.

Standard Reaction Conditions. Synaptic complexes were formed by mixing together 100 nM reactive ODN, 2 μM RecA protein and 10–100 nM dsDNA on ice and then increasing the temperature to 37° C. The reactions were conducted in 50 μL volumes and contained 10 mM trisacetate buffer (pH 7.5), 50 mM sodium acetate, 12 mM magnesium acetate, 1 mM DTT, 1 mM Γ-S-ATP and 5% glycerol. Alkylation of the dsDNA target by chlorambucil was allowed to go to completion by incubating the reactions for 6 hours at 37° C.

Assay of the Modification Products. To detect the sites of crosslinkage on dsDNA the reaction mixtures were diluted PAGE and sites of DNA cleavage were identified by comparison with the products obtained with Maxam and Gilbert reactions in accordance with the teachings of Maxam, A. M., & Gilbert, W. (1977) *Prog. Natl. Acad. Sci. U.S.A.* 74, 560, or with marker prepared by restriction endonuclease digestion.

Formula 2 below depicts the nucleotide sequence SEQ ID NO:13 of 272 bp amplicon identical to region 1523–1794 of pGEM-4Z plasmid DNA SEQ ID NO:13 1 CGGGAAGCTA GAGTAAGTAG TTCGCCAGTT AATAGTTTGC GCAACGTTGT 50
51TGCCATTGCT ACAGGCATCG TGGTGTCACG CTCGTCGTTT GGTATGGCTT 100
101CATTCAGCTC CGGTTCCCAA CGATCAAGGC GAGTTACATG ATCCCCCATG 150
151TTGTGCAAAA AAGCGGTTAG CTCCTTCGGT CCTCCGATCG TTGTCAGAAG 200
201TAAGTTGGCC GCAGTGTTAT CACTCATGGT TATGGCAGCA CTGCATAATT 250
251CTCTTACTGT CATGCCATCC GT Formula 2

Table 1 below summarizes the results of the above-noted in vitro experiments. The Table shows the sequence of the 272 bp amplicon SEQ ID NO:13 in a region of homology with oligonucleotide reagents. Sequences of reactive oligonucleotides are shown below and are numbered 1, 1a and 2–12 (non-homologous regions are shown in underline type. U* denotes 5-(3-aminopropyl)-2'-deoxyuridine residues with attached chlorambucil moiety, 5'Chlb—denotes a chlorambucil moiety attached to the 5'-phosphate of an oligonucleotide through a 6-aminohexyl linker.

TABLE 1

| | 150 | 200 |
|---|---|---|

SEQ ID NO:29 5' . . . CCCCCATGTTGTGCAAAAAAGCGGTTAGCTCCTTCGGTCCTCCGATCGTTGTCAGAAGTAAGTTGGCCGCA . . . 3'
3' . . . GGGGGTACAACACGTTTTTTCGCCAATCGAGGAAGCCAGGAGGCTAGCAACAGTCTTCATTCAACCGGCGT . . . 5'

| ODN | Sequence | Length | Cross link % |
|---|---|---|---|
| SEQ ID NO:14 1 | 5'-ATGTTGTGCAAAAAAGCGGTTAGCTCCTTCGGTCCU*CCGATCGTTGTCAG | 50 | 56 |
| SEQ ID NO:15 1a | 5'Ch1b-ATGTTGTGCAAAAAAGCGGTTAGCTCCTTCGGTCCT CCGATCGTTGTCAG | 50 | ~10 |
| SEQ ID NO:15 1b | 5'-ATGTTGTGCAAAAAAGCGGTTAGCTCCTTCGGTCCT CCGATCGTTGTCAG | 50 | — |
| SEQ ID NO:16 2 | 5'-AAAAAGCGGTTAGCTCCTTCGGTCCU*CCGATCGTTGTCAG | 40 | 43 |
| SEQ ID NO:17 3 | 5'-TAGCTCCTTCGGTCCU*CCGATCGTTGTCAG | 30 | 38 |
| SEQ ID NO:18 4 | 5'-GGTCCU*CCGATCGTTGTCAG | 20 | 1 |
| SEQ ID NO:19 5 | 5'-<u>CCACCACATCGCCGCATAACCGAT</u>CCCTTCGGTCCU*CCGATCGTTGTCAG | 50 | 2 |
| SEQ ID NO:20 6 | 5'-ATGTTGTGCAAAAAAGCGGTTAGCT<u>TTCCTAACTTU*TTACCTACCACTGA</u> | 50 | 1 |
| SEQ ID NO:21 7 | 5'-<u>CCACCACATCGCCGCATAAC</u>TAGCTCCTTCGGTCCU*CCGATCGTTGTCAG | 50 | 6 |
| SEQ ID NO:22 8 | 5'-ATGTTGTGCAAAAAAGCGGTTAGCTCCTTC<u>AACTTU*TTACCTACCACTGA</u> | 50 | <1 |
| SEQ ID NO:23 9 | 5'-AAAAGCGGTTAGCTCCTTCGGTCCU*CCGATCGTTGTCAGAAGTAAGTTG | 49 | 52 |
| SEQ ID NO:24 10 | 5'-AAAAGCGGTTAGCTCCTTCG<u>ACCCU*CC</u>ACTCGTTGTCAGAAGTAAGTTG | 49 | 2 |
| SEQ ID NO:25 11 | 5'-AAAAGCGGTTAGCTCCTTCG<u>ACTCU*CTACT</u>CGTTGTCAGAAGTAAGTTG | 49 | <1 |
| SEQ ID NO:26 12 | 5'-AAAAGCGGTTAGCTCCTTCG<u>ACTTU*TTACT</u>CGTTGTCAGAAGTAAGTTG | 49 | <1 | two times with buffer containing 0.5% SDS and 200 μg/mL proteinase K. After 30 min incubation at 37° C. samples were extracted once with phenolchloroform, three times with ether and precipitated by ethyl alcohol. To introduce a nick at the positions of alkylated guanosines, DNA pellets were treated with 10% piperidine for 30 min at 95° C. Samples were precipitated again with ethyl alcohol and the DNA was collected by centrifugation, dried and dissolved in 80% formamide containing 0.1% xylene cyanol and bromophenol blue. Samples were analyzed by 8% denaturing As it can be seen from Table 1, ODN 1 has 50 nucleotide units and these are homologous to a matching sequence in the 272 base pair (bp) amplicon. The cross-linking function is attached to a 2'-deoxyuridine which is within the homologous sequence. It was found experimentally that ODN 1 binds to the amplicon and cross-links with one of the guanines immediately flanking the adenine to which the modified deoxyuridine bearing the cross-linking agent is base paired. ODN 1a also has 50 nucleotide units homologous to the amplicon, and has the cross-linking function at its 5' end. ODN 1a also binds and cross-links to the amplicon to a guanine which is in the immediate vicinity of the binding site of the 5' end of ODN 1a. ODN 2 is similar to ODN 1 (has an internal U*) but comprises of only 40 homologous nucleotides. ODN 2 also cross-links with the amplicon, and so does ODN 3 which has 30 homologous nucleotides and an internally located cross-linking function (U*). ODN 4 has only 20 homologous nucleotides and an internally located cross-linking function. ODN 4 does not cross-link to the amplicon, or cross-links only very poorly. ODN 5 has 50 nucleotide units, but only 25 are homologous to the amplicon. The internal cross-linking agent is within the homologous sequence, and ODN 5 cross-links only very poorly. This demonstrates that more than 25 homologous nucleotides are needed for significant cross-linking. ODN 6 has 25 homologous nucleotides but the cross-linking function is not within the homologous region. ODN 6 does not cross-link or cross-links only very poorly. ODN 7 has 30 homologous nucleotides in sequence, and the cross-linking function is in the homologous region. ODN 7 cross-links demonstrably, despite the presence of a sequence of 20 non-homologous nucleotides. ODN 8 has 30 homologous and 20 non-homologous nucleotides, each in a continuous sequence. The cross-linking agent is in the non-homologous sequence and ODN 8 does not cross-link. ODN 9 has 49 homologous units in sequence and cross-links. ODNs 10–12 each have only a few non-homologous nucleotides, but the non-homologous units are located close (next to or within 1 and 2 units respectively) to the nucleotide bearing the cross-linking function. ODNs 10–12 do not cross-link, or cross-link only very poorly.

In related experiments the ODNs designated ODN 1 and 1a in Table 1 were incubated with the 272 bp amplicon under the above described conditions but in the absence of recombinase enzyme. No cross-linking was observed in these experiments. In still related experiments the efficacy of the cross-linking between internally located cross-linking function (ODN 1 of Table 1) and terminally located cross-linking function (ODN 1a of Table 1) was compared by examining the intensity of the appropriate bands obtained in PAGE electrophoresis, pursuant to the Maxam Gilbert sequencing method. The internally located cross-linking function was found to be approximately 7 times more effective than the terminally located cross-linking function.

In Vitro and In Vivo Cross-linking with Human Genomic DNA

The ODNs used in these experiments were a 50mer and a 30 mer of the following structures:

50-mer: SEQ ID NO:27 GGTTATTTTTGAAGATA CGAATTTCU*CCAGAGACACAGCAGGATTTGTCA-HEXANOL 30-mer: SEQ ID NO:28 GAAGATACGAA TTTCU*CCAGAGACACAGCA-HEXANOL In these structures U* denotes 5-(3-aminopropyl)-2'-deoxyuridine residues with an attached chlorambucil moiety. These ODNs are complementary to the coding strand of a HLA DQB1 allele 0302 (nucleotides 815–864 and 825–854 according to Larhammar, D. et al. (1983) *Proc. Natl. Acad. Sci. U.S.A.* 80, 7313–7317.

In the in vitro experiment, cross-linking oligonucleotides were added to the naked human genomic DNA with or without recombinase enzyme (RecA from *Escherichia coli*).

Experimental description

Reagents were mixed to give final concentrations of genomic DNA—40 µg/ml; crosslinking ODN—5×10$^{-7}$M; RecA=2×10$^{-6}$M; MgCl$_2$—12 mM; ATP gamma-S—1 mM. In the control reactions the presence of either RecA or oligonucleotides was omitted. The solutions were incubated at 37° C. for 3 hours, then deproteinized with Proteinase K/SDS for 30 minutes at 37° C. DNA was recovered by phenol:chloroform extraction and treated with 1M pyrrolidine at 90° C. for 30 minutes to cleave the DNA at the crosslinking sites. The DNA was precipitated by ethanol and the Ligation-Mediated PCR reaction was performed as described by Chong-Soon Lee et.al. (Biochemistry 1994, 33, 6024–6030) to visualize nicks caused by alkylation at crosslinking sites.

The results of this experiment, as observed on PAGE electrophoresis, were that binding of the 50 mer and of the 30 omer to the matching sequence in the human genomic allele and subsequent cross-linking had occurred, but only when the ODN and the recombinase enzyme were both present in the incubation mixture. This experiment proves site specific alkylation (cross-linking with the ODN) of whole human genomic DNA in vitro with the ODN of the invention that is complementary in the Watson Crick sense to a sequence in the double stranded genomic DNA.

In an in vivo cell culture experiment the 50 mer and the 30 mer ODNs were added to the culture of BSM B-lymphocyte cells under conditions described below.

Experimental Description

BSM B-lymphocyte cells were grown in a 25 ml flask to a density of 4.5×10$^6$ cells per ml. Media:

500 ml RPMI 1640 with L-glutamine (2 mM) (Gibco BRL Cat. No. 11875-036)

50 ml of HI-FCS (fetal calf serum: Gibco BRL Cat. No. 26140, heat inactivated 30' at 55° C.)

5 ml of 100× Penn/Strep (Gibco BRL Cat. No. 15070-022)

5 ml of 200 mM L-Glutamine (Gibco BRL Cat. No. 25030-024)

5 ml of 100× Sodium Pyruvate (11 mg/ml filter sterilized) of 1M HEPES, pH 7.3 (Gibco BRL Cat. No. 15630-023).

For each treatment, 2 ml was taken from a BSM cell flask (25 ml) and was spun 5 minutes at 1,200 rpm, then resuspended in:

| ODN NAME | ODN Conc (µM) | µl serum-free media | µl ODN (from water 10$^{-4}$M in water) | |
|---|---|---|---|---|
| 24.01 (50-mer) | 0 | 160 | 0 | 40 |
| 24.01 (50-mer) | 1 | 160 | 2 | 38 |
| 24.01 (50-mer) | 10 | 160 | 20 | 20 |
| 24.01 (50-mer) | 50 | 160 | 20 (from 5 × 10$^{-4}$M) | 20 |

Note: Serum free media is identical to the above media except for the absence of 50 ml of HI-FCS (Gibco BRL Cat. No. 26140, heat inactivated 30 min at 55° C.).

Each sample was incubated for 3.5 hours at 37° C. and 5% CO$_2$ in a 48-well microtiter plate. Cells were transferred to 1.5 ml plastic centrifuge tubes, pelleted 5' at 2,000 rpm, washed twice with 500 µl PBS and deproteinized with Proteinase K/SDS overnight at 37° C. DNA was recovered by phenol:chloroform extraction and Rnase A digestion and treated with 1M pyrrolidine at 90° C. for 30 min to cleave DNA at the crosslinking sites. Pyrrolidine was removed by ethanol precipitation and the Ligation-Mediated PCR reaction was performed as described by Chong-Soon Lee et. al. (supra) to visualize nicks caused by alkylation.

The foregoing experiments showed that the 50 mer and the 30 mer ODN sequence specifically bound to and alkylated (cross-linked) the 0302 allele in the human genomic DNA.

In light of the foregoing, a general structure of the oligonucleotides of the present invention is given by Formula 3

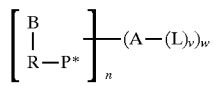

Formula 3 where B—R—P* represents a nucleotide building block of the oligonucleotide which may optionally bear a reporter group or may optionally include a radioactive label. B—R—P* includes intermediate nucleotide units and the 5'- and 3' terminal nucleotide units. Specifically, B represents a heterocyclic base component of the nucleotide, R represents a sugar moiety which forms a pyranose or furanose ring, or an isosteric analog thereof, and P* represents a phosphate group including a phosphate monoester, phosphate diester or phospate triester group, or P* represents a monothioate or dithioate analog of said phosphate groups. P* further includes the above-noted phosphate, phosphothioate or phosphodithioate groups in internucleotidic linkages, and also at the 5' and 3' terminus of the oligonucleotide. The $(A-(L)_v)_w$ grouping forms an electrophilic alkylating group such that L is a leaving group and $A-(L)_v$ is inert under conditions of hybridization with the target sequence of DNA or RNA, in the sense that the group A—L reacts only after hybridization with the target sequence. n is an integer with the values between 5 and approximately 3000; v is 1 or 2; and w is between 1–10, and the oligonucleotide includes a sequence which is complementary in the Watson Crick, Hoogsteen or reverse Hoogsteen sense to a target sequence of single or double stranded DNA or single stranded RNA.

What is claimed is:

1. A process for cross-linking with a target sequence in double stranded DNA, the process comprising:
   contacting in the presence of a recombinase enzyme the double stranded DNA having the target sequence with an oligonucleotide of the formula

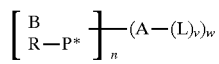

where B—R—P* represents a nucleotide building block of the oligonucleotide which is substituted or unsubstituted with a reporter group and lacks or includes a radioactive label; B in said B—R—P* represents a heterocyclic base component of the nucleotide, R in said B—R—P* is selected from 2-deoxyribofuranosyl, 2-O-alkylribofuranosyl, and 2-deoxy-2-fluororibofuranosyl, and P* in said B—R—P* represents a phosphate group including a phosphate monoester, phosphate diester or phospate triester group, or P* represents a monothioate or dithioate analog of said phosphate groups;
   (A—(L)$_v$)$_w$ represents an electrophilic alkylating group wherein L is a leaving group, A is a group that covalently links L to the oligonucleotide and A—L is substantially inert in a cross-linking reaction under conditions that permit hybridization with the target sequence of double stranded DNA, and A—L reacts substantially only after hybridization with the target sequence has occurred;
   n is an integer with the values between 26 and approximately 300,
   v is 1 or 2;
   w is between 1–10,
   and the oligonucleotide includes a continuous sequence of at least approximately 26 nucleotide units which sequence is complementary in the Watson Crick sense to the a target sequence in the double stranded DNA, and wherein at least one A—(L)$_n$ group is covalently attached to the continuous sequence that is complementary to the target sequence.

2. The process of claim 1 which is performed in vitro.

3. The process of claim 1 wherein the oligonucleotide has no more than approximately 60 nucleotide units.

4. The process of claim 1 wherein the A—(L)$_v$ is a group selected from the groups consisting of
   —(CH$_2$)$_q$—Y—(CH$_2$)$_m$—L, (CH$_2$)$_q$—CO—CH$_2$—L,
   —(CH$_2$)$_q$—NH—CO—(CH$_2$)$_m$—(X)$_{n'}$—N(R$_1$)—(CH$_2$)$_p$—L, and
   —(CH$_2$)$_{q'}$—O—(CH$_2$)$_{q''}$—NH—CO—(CH$_2$)$_m$—(X)$_n$, —N(R$_1$)—(CH$_2$)$_p$—L where each of m and q is independently 0 to 8, inclusive, q' is 3 to 7 inclusive, q" is 1 to 7 inclusive, Y is a linking group derived from a bifunctional molecule having a hydrocarbyl backbone and having at each end a functionality selected from —NH$_2$, —OH, SH, —COOH and C≡CH, and X is phenyl, or phenyl substituted with chloro, bromo, lower alkyl or lower alkoxy groups, n' is 0 or 1, p is an integer from 1 to 6, and R$_1$ is H, lower alkyl or (CH$_2$)$_p$—L.

5. The process of claim 1 wherein the A—(L)$_v$ group is selected from the groups consisting of
   —(CH$_2$)$_3$O(CH$_2$)$_2$NHCO(CH$_2$)$_3$—C$_6$H$_4$—N—(CH$_2$CH$_2$Cl)$_2$
   —(CH$_2$)$_3$NHCO(CH$_2$)$_3$—C$_6$H$_4$—N—(CH$_2$CH$_2$Cl)$_2$, and
   —(CH$_2$)$_6$NHCO(CH$_2$)$_3$—C$_6$H$_4$—N—(CH$_2$CH$_2$Cl)$_2$.

6. The process of claim 4 wherein the A—(L)$_v$ group is covalently attached to a nucleotide unit which is internal within the continuous sequence that is complementary to the target sequence of double stranded DNA.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CTGGATGTUC CTTC    1 4

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

AGACAGCACA GAATTCGAAG GAACATCCAG    3 0

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

ACCGTCCTTG ACACGATGGA CTCC    2 4

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CTCCAUCGTG TCAAG    1 5

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

NAGAGGAGAA AGGAGAGAGN     20

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:6:

ATATAAGGAG AGAGGAAAGA GGAGACAAA     29

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TTGTGGTGGT YGTGTYGTGG TGGG     24

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:8:

GGGAGGAGCA GAGGAGGAGG AGAA     24

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TTTTCTTTTY GGGGGTN     17

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:10:

TTTTTAAAAG AAAAGGGGGG ACTGG     25

( 2 ) INFORMATION FOR SEQ ID NO:11:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:11:

NCTTTCCTCT CTTTTCCCCN                                                                            20

( 2 ) INFORMATION FOR SEQ ID NO:12:

( i ) SEQUENCE CHARACTERISTICS:
    ( A ) LENGTH: 40 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:12:

AAATACTGGG AGAAAGGAGA GAAAAGGGGA CCCAACGTAT                                                      40

( 2 ) INFORMATION FOR SEQ ID NO:13:

( i ) SEQUENCE CHARACTERISTICS:
    ( A ) LENGTH: 272 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:13:

CGGGAAGCTA GAGTAAGTAG TTCGCCAGTT AATAGTTTGC GCAACGTTGT TGCCATTGCT                                 60

ACAGGCATCG TGGTGTCACG CTCGTCGTTT GGTATGGCTT CATTCAGCTC CGGTTCCCAA                                120

CGATCAAGGC GAGTTACATG ATCCCCCATG TTGTGCAAAA AAGCGGTTAG CTCCTTCGGT                                180

CCTCCGATCG TTGTCAGAAG TAAGTTGGCC GCAGTGTTAT CACTCATGGT TATGGCAGCA                                240

CTGCATAATT CTCTTACTGT CATGCCATCC GT                                                             272

( 2 ) INFORMATION FOR SEQ ID NO:14:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

ATGTTGTGCA AAAAAGCGGT TAGCTCCTTC GGTCCUCCGA TCGTTGTCAG                                           50

( 2 ) INFORMATION FOR SEQ ID NO:15:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

ATGTTGTGCA AAAAAGCGGT TAGCTCCTTC GGTCCTCCGA TCGTTGTCAG                                           50

( 2 ) INFORMATION FOR SEQ ID NO:16:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

AAAAAGCGGT TAGCTCCTTC GGTCCUCCGA TCGTTGTCAG 40

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

TAGCTCCTTC GGTCCUCCGA TCGTTGTCAG 30

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GGTCCUCCGA TCGTTGTCAG 20

( 2 ) INFORMATION FOR SEQ ID NO:19:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

CCACCACATC GCCGCATAAC CGATCCCTTC GGTCCUCCGA TCGTTGTCAG 50

( 2 ) INFORMATION FOR SEQ ID NO:20:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

ATGTTGTGCA AAAAGCGGT TAGCTTTCCT AACTTUTTAC CTACCACTGA 50

( 2 ) INFORMATION FOR SEQ ID NO:21:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

CCACCACATC GCCGCATAAC TAGCTCCTTC GGTCCUCCGA TCGTTGTCAG 50

( 2 ) INFORMATION FOR SEQ ID NO:22:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

ATGTTGTGCA AAAAAGCGGT TAGCTCCTTC AACTTUTTAC CTACCACTGA 50

( 2 ) INFORMATION FOR SEQ ID NO:23:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

AAAAGCGGTT AGCTCCTTCG GTCCUCCGAT CGTTGTCAGA AGTAAGTTG 49

( 2 ) INFORMATION FOR SEQ ID NO:24:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

AAAAGCGGTT AGCTCCTTCG ACCCUCCACT CGTTGTCAGA AGTAAGTTG 49

( 2 ) INFORMATION FOR SEQ ID NO:25:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

AAAAGCGGTT AGCTCCTTCG ACTCUCTACT CGTTGTCAGA AGTAAGTTG 49

( 2 ) INFORMATION FOR SEQ ID NO:26:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

AAAAGCGGTT AGCTCCTTCG ACTTUTTACT CGTTGTCAGA AGTAAGTTG 49

( 2 ) INFORMATION FOR SEQ ID NO:27:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

GGTTATTTTT GAAGATACGA ATTTCUCCAG AGACACAGCA GGATTTGTCA 50

( 2 ) INFORMATION FOR SEQ ID NO:28:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

GAAGATACGA ATTTCUCCAG AGACACAGCA 30

(2) INFORMATION FOR SEQ ID NO:29:

(i) SEQUENCE CHARACTERISTICS:
      (A) LENGTH: 71 base pairs
      (B) TYPE: nucleic acid
      (C) STRANDEDNESS: double
      (D) TOPOLOGY: linear (xi) SEQUENCE DESCRIPTION: SEQ ID NO:29:

```
CCCCCATGTT  GTGCAAAAAA  GCGGTTAGCT  CCTTCGGTCC  TCCGATCGTT  GTCAGAAGTA        60
AGTTGGCCGC  A                                                                 71
```